(12) United States Patent
Khajavi et al.

(10) Patent No.: US 10,413,378 B2
(45) Date of Patent: Sep. 17, 2019

(54) SAFETY-BLADE DISPENSER AND RELATED METHODS

(71) Applicant: STARTBOX, LLC, Atlanta, GA (US)

(72) Inventors: Kaveh Khajavi, Atlanta, GA (US); David E. Lane, II, Falkville, AL (US); Luke Boland, Englewood, CO (US); Christopher Davis, Arlington, VA (US); John G. Kerwood, Canton, GA (US)

(73) Assignee: STARTBOX, LLC, Atlanta, GA (US)

( * ) Notice: Subject to any disclaimer, the term of this patent is extended or adjusted under 35 U.S.C. 154(b) by 0 days.

(21) Appl. No.: 15/587,130

(22) Filed: May 4, 2017

(65) Prior Publication Data

US 2017/0360523 A1 Dec. 21, 2017

Related U.S. Application Data

(60) Provisional application No. 62/331,790, filed on May 4, 2016, provisional application No. 62/331,819, filed
(Continued)

(51) Int. Cl.
*B65D 83/10* (2006.01)
*A61B 17/32* (2006.01)
(Continued)

(52) U.S. Cl.
CPC ...... *A61B 50/3001* (2016.02); *A61B 17/3215* (2013.01); *A61B 17/3217* (2013.01);
(Continued)

(58) Field of Classification Search
CPC .......... A61B 50/3001; A61B 2050/314; A61B 17/3211; B65D 83/10
(Continued)

(56) References Cited

U.S. PATENT DOCUMENTS

| | | | | |
|---|---|---|---|---|
| 909,110 | A | * 1/1909 | O'Neil | B65D 83/10 221/232 |
| 2,109,017 | A | * 2/1938 | Rodrigues | B65D 83/10 206/356 |

(Continued)

FOREIGN PATENT DOCUMENTS

| | | |
|---|---|---|
| WO | 2015103279 A1 | 7/2015 |
| WO | 2017059452 A1 | 4/2017 |

OTHER PUBLICATIONS

International Search Report and Written Opinion issued in International Application No. PCT/US2016/055210 dated Mar. 13, 2017.

*Primary Examiner* — Jacob S. Scott
*Assistant Examiner* — Ayodeji T Ojofeitimi
(74) *Attorney, Agent, or Firm* — Meunier Carlin & Curfman LLC

(57) ABSTRACT

Safety-blade dispensers for safely storing surgical blades prior to surgery and optionally for retrieving used surgical blades after surgery. In either case, the safety-blade dispenser is configured to store one or more surgical blades in an orientation that allows a user to simply and safely attach a surgical tool handle to the surgical blades (and optionally remove the handle from the surgical blades) without requiring the user to physically touch or manipulate the surgical blades by hand. The safety-blade dispensers disclosed herein may be used alone or in conjunction with a system and method of preventing wrong-site surgery.

19 Claims, 34 Drawing Sheets

Related U.S. Application Data on May 4, 2016, provisional application No. 62/332,330, filed on May 5, 2016.

(51) Int. Cl.
| | |
|---|---|
| *A61B 50/30* | (2016.01) |
| *A61B 17/3215* | (2006.01) |
| *A61B 17/3217* | (2006.01) |
| *A61B 50/20* | (2016.01) |
| *A61B 50/36* | (2016.01) |
| *A61B 90/96* | (2016.01) |
| *A61B 90/94* | (2016.01) |
| *A61B 17/3211* | (2006.01) |
| *A61B 50/00* | (2016.01) |
| *A61B 90/00* | (2016.01) |

(52) U.S. Cl.
CPC ............ *A61B 50/20* (2016.02); *A61B 50/362* (2016.02); *A61B 90/94* (2016.02); *A61B 90/96* (2016.02); *B65D 83/10* (2013.01); *A61B 17/3211* (2013.01); *A61B 2050/008* (2016.02); *A61B 2050/0059* (2016.02); *A61B 2050/314* (2016.02); *A61B 2090/0807* (2016.02)

(58) Field of Classification Search
USPC ................. 221/133, 209, 270; 206/350–370
See application file for complete search history.

(56) References Cited

U.S. PATENT DOCUMENTS

| | | | | |
|---|---|---|---|---|
| 2,624,453 | A * | 1/1953 | Muros | B65D 83/10 221/232 |
| 2,653,704 | A * | 9/1953 | Nelson | B65D 83/10 206/355 |
| 3,080,998 | A * | 3/1963 | La Cas | B65D 83/10 221/232 |
| 3,093,266 | A * | 6/1963 | Kuhnl | B65D 83/10 221/102 |
| 3,244,317 | A * | 4/1966 | Raybin | A61B 17/3213 206/355 |
| 3,542,245 | A * | 11/1970 | Braginetz | A47F 1/08 221/232 |
| 3,848,770 | A * | 11/1974 | Iten | B65D 83/10 221/102 |
| 3,910,455 | A * | 10/1975 | Ferraro | B65D 83/10 221/102 |
| 4,106,620 | A | 8/1978 | Brimmer et al. | |
| 4,395,807 | A * | 8/1983 | Eldridge, Jr. | A61B 17/3217 206/355 |
| 4,826,042 | A * | 5/1989 | Vujovich | B65D 83/10 206/208 |
| 4,850,512 | A * | 7/1989 | Vujovich | B65D 83/10 206/355 |
| 4,903,390 | A * | 2/1990 | Vidal | A61B 17/3217 206/355 |
| 5,088,173 | A * | 2/1992 | Kromer | A61B 17/3217 206/355 |
| 5,181,609 | A * | 1/1993 | Spielmann | A61B 50/362 206/366 |
| 5,251,783 | A * | 10/1993 | Gringer | B65D 83/10 221/102 |
| 5,257,692 | A * | 11/1993 | Heacox | A01N 1/02 206/210 |
| 5,662,221 | A * | 9/1997 | Abidin | A61B 17/3215 206/352 |
| 5,727,682 | A * | 3/1998 | Abidin | A61B 17/3215 206/354 |
| 5,875,532 | A * | 3/1999 | Musgrave | A61B 17/3215 206/355 |
| 5,894,925 | A * | 4/1999 | Sukiennik | A61B 17/3217 206/356 |
| 5,938,027 | A * | 8/1999 | Soroff | A61B 17/3213 206/355 |
| 6,158,616 | A * | 12/2000 | Huang | B65D 83/10 221/102 |
| 6,216,868 | B1 * | 4/2001 | Rastegar | A61B 17/3215 206/356 |
| 6,874,629 | B1 * | 4/2005 | Wortrich | A61B 17/3215 206/349 |
| 7,398,880 | B2 * | 7/2008 | Henry | A61B 17/3217 206/355 |
| 2004/0178214 | A1 * | 9/2004 | Wei | B25H 3/00 221/247 |
| 2007/0039844 | A1 * | 2/2007 | Zyzelewski | B65D 43/163 206/363 |
| 2009/0018864 | A1 | 1/2009 | Gecelter | |
| 2010/0170913 | A1 * | 7/2010 | Shoshani | A47K 10/426 221/44 |
| 2011/0015938 | A1 | 1/2011 | Rabinowitz et al. | |
| 2011/0233229 | A1 * | 9/2011 | Schekalla | B65D 83/0829 221/270 |
| 2013/0126550 | A1 * | 5/2013 | Schneider | B65D 83/10 221/270 |
| 2013/0159015 | A1 | 6/2013 | O'Con | |
| 2014/0034665 | A1 * | 2/2014 | Walter | B65D 83/08 221/102 |
| 2014/0110298 | A1 * | 4/2014 | Khajavi | A61B 19/56 206/438 |
| 2014/0263393 | A1 * | 9/2014 | Garavaglia | B65D 83/10 221/133 |
| 2016/0304269 | A1 * | 10/2016 | Erdmann | B65D 83/0817 |
| 2017/0174412 | A1 * | 6/2017 | Wonderley | B65D 83/10 |

* cited by examiner

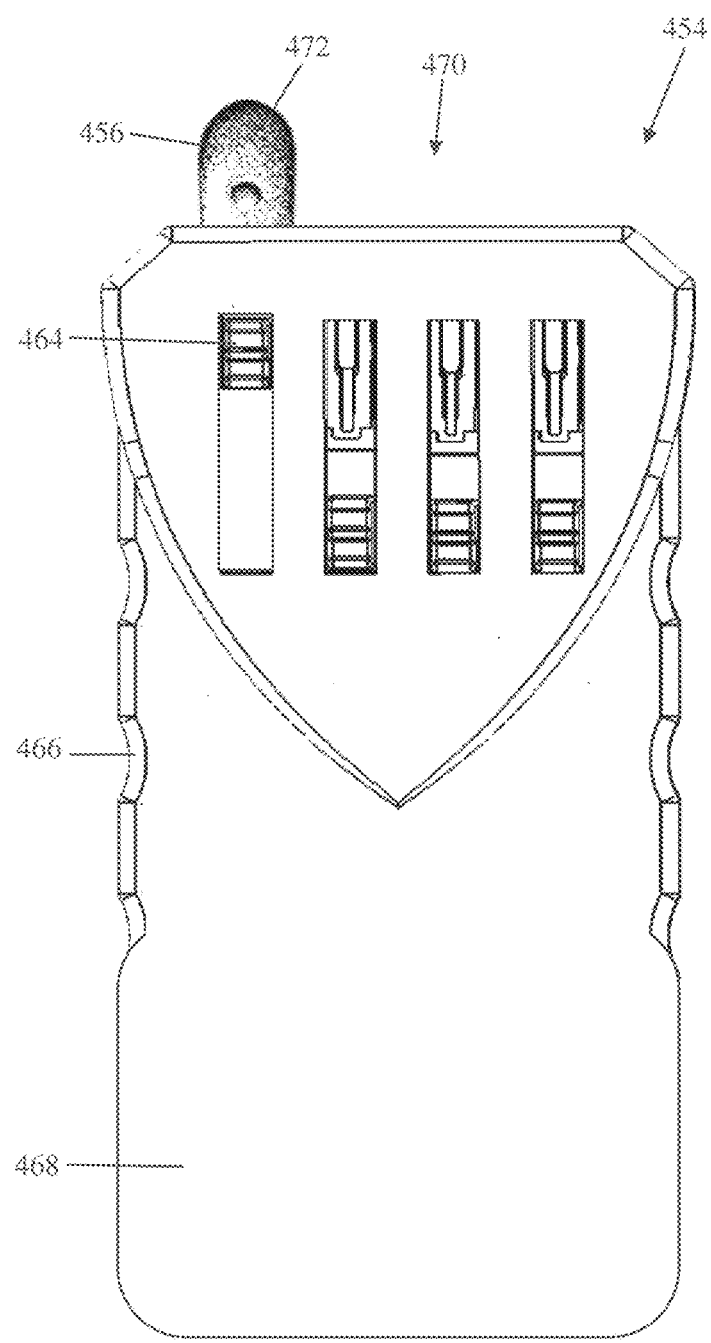
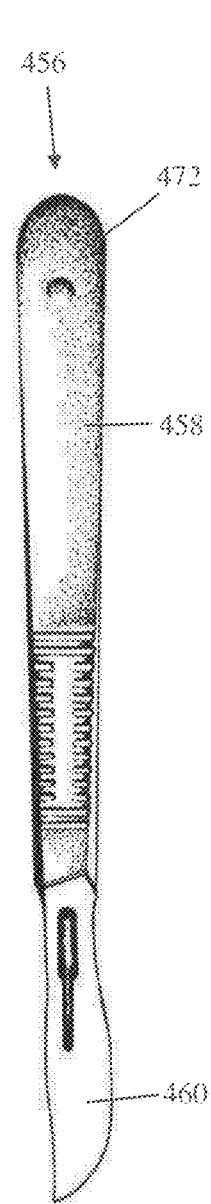
Fig. 26
Fig. 27

SAFETY-BLADE DISPENSER AND RELATED METHODS

CROSS-REFERENCE TO RELATED APPLICATION

In accordance with 37 C.F.R 1.76, a claim of priority is included in an Application Data Sheet filed concurrently herewith. The present invention claims priority to U.S. Provisional Patent App. No. 62/331,790 filed May 4, 2016 entitled "SAFETY BLADE CONTAINER", U.S. Provisional Patent App. No. 62/332,330 filed May 5, 2016 entitled "SAFETY BLADE CONTAINER", and U.S. Provisional Patent App. No. 62/331,819 filed May 4, 2016 entitled "SYSTEM AND METHOD FOR PREVENTING WRONG-SITE SURGERIES." The contents of each of the above referenced applications are herein incorporated by reference in its entirety.

FIELD OF THE INVENTION

The present invention relates generally to surgery and, more specifically, safety blade containers for use in dispensing surgical blades for use in surgical procedures and optionally retrieving used surgical blades after surgical procedures, wherein the safety blade containers may be used as part of a system for preventing wrong-site surgeries.

BACKGROUND OF THE INVENTION

A persistent safety issue is that of needle-stick and other sharps-related injuries to OR personnel, including scalpel or blade-related injuries. The Center for Disease Control estimates that each year approximately 385,000 needle-stick and other sharps-related injuries (averaging over 1000 a day), of which blade-related injuries account for almost 10%. Scalpel blades are necessarily extremely sharp and, as a result, are more likely to penetrate the flesh of a surgeon or other OR personnel more deeply than needle-stick injuries. Blade-related injuries can therefore be monumental for OR personnel, including contracting diseases stemming from blood-borne pathogens such as HIV/AIDS, hepatitis-C, hepatitis-B, etc . . . , as well as the loss of income during recovery and rehabilitation and the potential loss of occupation due to permanent physical injuries (e.g. to the hand of a surgeon).

Wrong-site surgeries are also a persistent problem within the healthcare system. As defined by the Joint Commission on Accreditation of Healthcare Organizations (JCAHO), wrong-site surgery includes wrong side or site of the body, wrong procedure, and wrong-patient surgeries. A multitude of factors have been identified that may contribute to an increased risk of wrong-site surgery. Despite the implementation of strategies to prevent wrong patient, wrong site, wrong side surgery, regrettably this seemingly most preventable of complications still occurs. The incorrect assumption of a medical professional's infallibility, coupled with organized medicine's focus on the individual's medical mistakes rather than a systems approach have contributed to this problem.

In an attempt to improve patient safety, compliance with the *Universal Protocol for Preventing Wrong Site, Wrong Procedure, Wrong Person Surgery* is required of all Joint Commission accredited organizations. As a part of the universal protocol, a "pause" or "time out" is required. This serves as a final verification of: (1) the correct patient; (2) the correct procedure, site and side; and as applicable, (3) the availability of implants or instrumentation, prior to making incision. This is a time when all members of the surgical team are supposed to pause to review the case, and agree that the correct procedure is being done on the correct patient, at the correct site, and on the correct side. In theory, this would ensure that any errors that had been made could be detected prior to incision. In reality, the "time out" seldom occurs; and when it does, not in any uniform or regular manner. Without a uniform or regular procedure, ritualized compliance, i.e. going through the motions, results in many institutions. The universal protocol cannot enforce a pause, and does not specify a protocol as to what should happen during a pause. The universal protocol does not specify a particular time for the pause to occur, and it does not specify a protocol as to what should happen during the pause; that is to say, what information should be communicated by whom, and to whom. While guidelines may be suggested, each institution determines how to comply, therefore standardization is not achieved.

The present invention is directed at addressing the unmet needs of preventing or reducing blade-related injuries to OR personnel, including doing so while also preventing or reducing wrong-site surgeries.

SUMMARY OF THE INVENTION

The present invention addresses the unmet needs described above by providing a variety of safety-blade dispensers suitable for use independently from or in conjunction with a system and method for preventing wrong-site surgeries such as that shown and described in commonly owned and co-pending International Patent Application PCT/US16/55210 (filed 3 Oct. 2016) entitled "System and Method for Preventing Wrong-Site Surgeries", published as WO2017-059452 on Apr. 6, 2017, the contents of which is hereby incorporated by reference as is set forth herein in its entirety ("the '210 PCT").

The system and method of the '210 PCT includes computer software system configured to provide a user with a method of preventing wrong site surgeries, in combination with any of the various safety blade-dispensers. The safety-blade dispensers can optionally include at least one component, such as a label, paper, or tape, which prevents or impedes a surgeon from accessing one or more surgical instruments stored within until after a "time-out" is performed by the surgeon or authorized OR personnel to confirm various details (e.g. correct patient, correct procedure, correct equipment, etc . . . ) before starting the intended surgical procedure. The computer software system can be run on any of a variety of computing devices, such as a computer (e.g. stationary desktop and/or laptop) and/or a hand-held computing device (e.g. smart-phones such as IPHONE and/or a tablet device such as an IPAD or SURFACE PRO) used within the medical environment. The "medical environment" includes anywhere along the continuum in which patient and medical team (including the doctor, office personnel, nurses, medical technicians, surgeons, administrators) interact, from the surgeon's office (where the initial consultation and decision for surgery is made) to the operating room (where the surgery takes place). The term may also include personnel involved with post-surgical data collection and/or analysis, such as (but not limited to) (a) insurance companies for the patient, hospital and/or surgeon, (b) state and/or federal agency departments/programs (e.g. Medicare/Medicaid) which reimburse funds to the hospital and/or surgeon, (c) any other agency (private and/or governmental) which generates payment to the patient, hospital and/or surgeon for the specific surgical case, and/or (d) quality control and/or hospital administration to identify areas of improvement and/or best practices.

The system and related methods of preventing wrong-site surgeries and blade-related injuries utilize computer software system to support and provide several functionalities, including but not necessarily limited to voice recording, recording playback, an electronic patient-identifying component (such as a patient ID band) capable of being scanned, safety blade-dispenser capable of being scanned, and any of a variety of analytics generated or based upon data acquired through the use of the system from "decision-to-incision", that is, from the decision to have surgery (made in the surgeon's office) through the actual surgery (in the OR). Scanning of the patient ID band and/or safety blade-dispenser may be accomplished by scanning functionality of the computer, hand-held device and/or scanning systems separate from the system that cooperate and communicate with the system. The system may use any of a variety of suitable biometric identification technologies (e.g. iris scan, finger-prints, genetics, etc . . . ) in order to identify the patient (and/or the guardian of the patient if the patient is a minor or incapacitated) at any point in the medical environment.

The safety blade-dispenser can include a variety of scalpel blades for the surgeon to select from in order to perform the first incision of the operation. The safety blade-dispenser (and/or label described below) can optionally be color-coded to indicate the laterality of the surgery (e.g. rose or red for "right" sided surgery, lavender for "left" sided surgery, and a neutral color (such as grey) for a surgery with no-laterality). The safety blade-dispenser can optionally include a label with a QR code capable of being scanned and linked with patient-data from the patient ID band via the software assembly to create a unique identifier for the particular safety-blade dispenser assigned to the patient during the pre-operative assessment in the hospital after admission on the day of surgery. This unique identifier ensures that the patient receives the correct type of blade-dispenser, meaning the correct laterality of the intended surgery, and can be tracked throughout the remainder of the medical environment and associated with any data captured throughout the entire medical environment to ensure it is correct and used to perform the intended surgery. The label can only be removed from the safety-dispenser after a timeout has been performed by the surgeon or authorized OR personnel. Once the label is removed, the surgeon then and only then has access to a variety of scalpel blades in the blade dispenser, the desired one of which can be safely advanced out of the dispenser for engagement to a handle such that the first incision can be made and the operation commenced.

The safety blade-dispenser can optionally be initially provided sealed in transparent double sterile packaging (which is then placed in a non-sterile container with a transparent window). The transparent packaging/window allows for the identifying information on the confirmation label (e.g. QR code and/or laterality indicator) to be scanned before the safety blade-dispenser is removed from any of the packaging. In this manner, one can avoid the need to have the same identifying information on multiple levels of the packaging. This reduces manufacturing costs and the complexity of matching multiple packaging components to ensure they all have the same identifying information, which would otherwise be required.

The system of preventing wrong-site surgeries and blade-related injuries allows for tracking of a variety of data from pre-hospitalization to the actual surgical procedure, which the software system can use to generate any of a variety of analytics. The analytics may be based upon, but not necessarily limited to, so-called "near miss" data (that is, errors that were caught and avoided during the use of the system), surgery type and laterality, surgical outcomes, surgical complications, patient demographics, geographic information, as well as the date, time, location and personnel associated with each interaction or use of the system for efficiency and accountability. For example, analytics based on "near miss" data may provide the hospital and/or insurers and/or quality improvement specialists valuable data as to where errors or possible errors may have occurred in order to drive remediation efforts to minimize or avoid such errors in the future. The analytics may also be used to identify best practices based on the data collected, either within the hospital system ("intra-system") and/or amongst multiple different hospital systems ("inter-system"), and assessed to identify best practices for further reducing wrong-site surgery errors.

The safety-blade dispensers disclosed herein are configured to store one or more surgical blades in an orientation that allows a user to simply and safely attach a surgical tool handle to the surgical blades without the need for user intervention with his/her hands. The dispenser may include a lock mechanism for securing the container closed, and may contain an electronic tracking mechanism. In addition to dispensing blades in a safe manner, the safety-blade dispensers of the present application may also have an optional blade removal feature to enable the removal of the blade after the surgical procedure without any manual touching of the blade by a user. By eliminating the need for a user to manually touch or manipulate the blade from the blade handle, the likelihood for inadvertent blade or needle-stick injuries is effectively minimized or reduced.

Accordingly, it is an objective of the invention to provide a container for safely dispensing surgical blades for use in surgery and optionally safely removing surgical blades after surgery.

It is a further objective of the invention to provide a container for safely dispensing surgical blades for use in surgery and optionally safely removing surgical blades after surgery wherein the surgical blades are in an orientation that allows a user to simply and safely attach a surgical tool handle to the surgical blade and optionally remove the surgical blade from the surgical tool handle without the user touching the surgical blades with his/her hand.

It is a further objective of the invention to provide any of a variety of safety-blade dispensers for use in systems and methods for preventing wrong-site surgeries with the ability to consistently produce, capture, and store reliable and mineable wrong site surgery data, electronic wrong site surgery near miss data, electronic wrong site surgery error data and/or an electronic patient surgical profile.

Other objectives and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

BRIEF DESCRIPTION OF THE FIGURES

FIG. 26 is a plan view of the safety blade-dispenser of FIG. 23 with one scalpel handle advanced to a removable position;

FIG. 27 is a plan view of one example of a scalpel suitable for use with the safety blade-dispenser of FIG. 23;

DETAILED DESCRIPTION OF THE INVENTION

Figure 1:
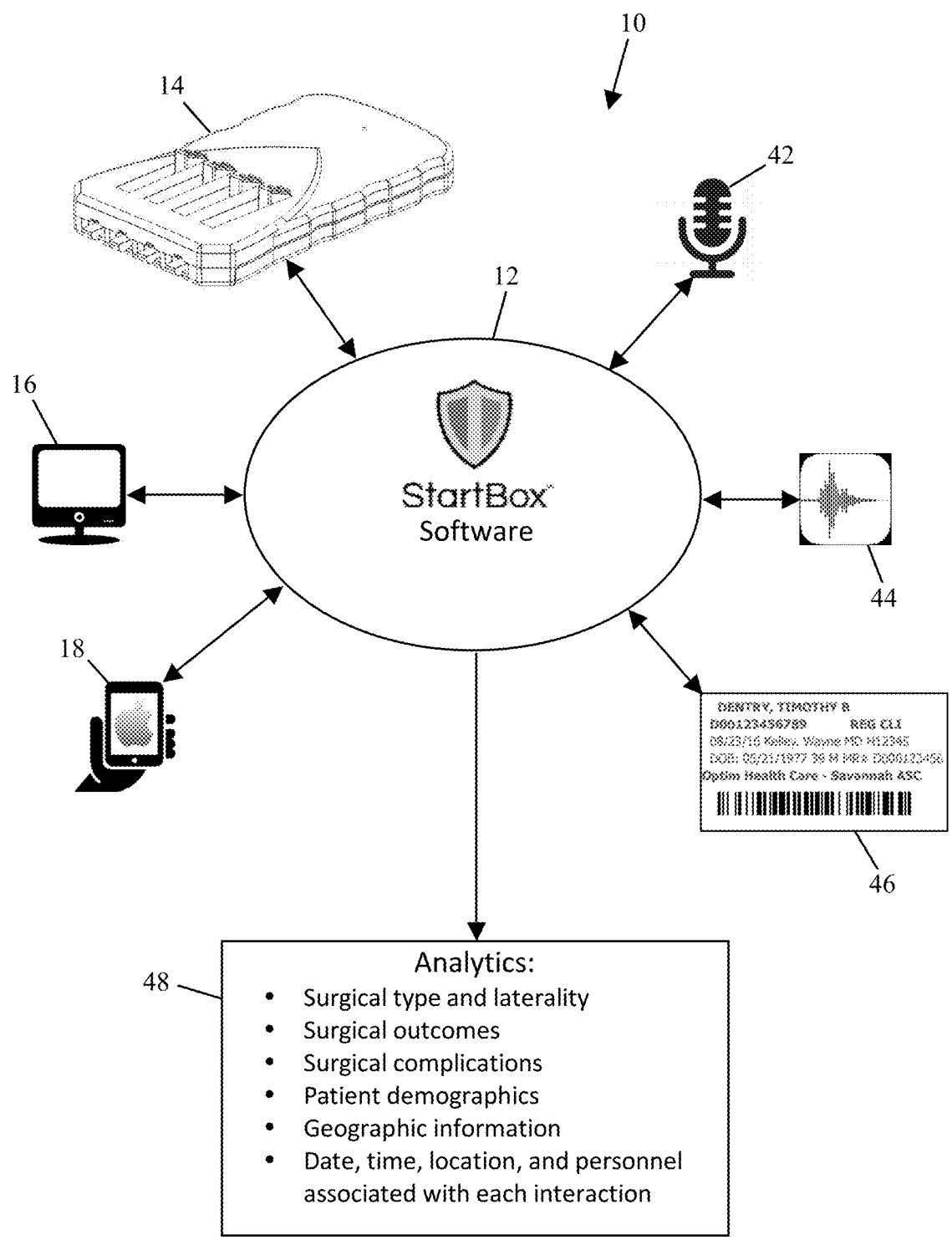
FIG. 1 is a graphical representation of an exemplary wrong-site surgery prevention system which may include any of the various safety-blade dispensers of the present disclosure.
Figure 2:
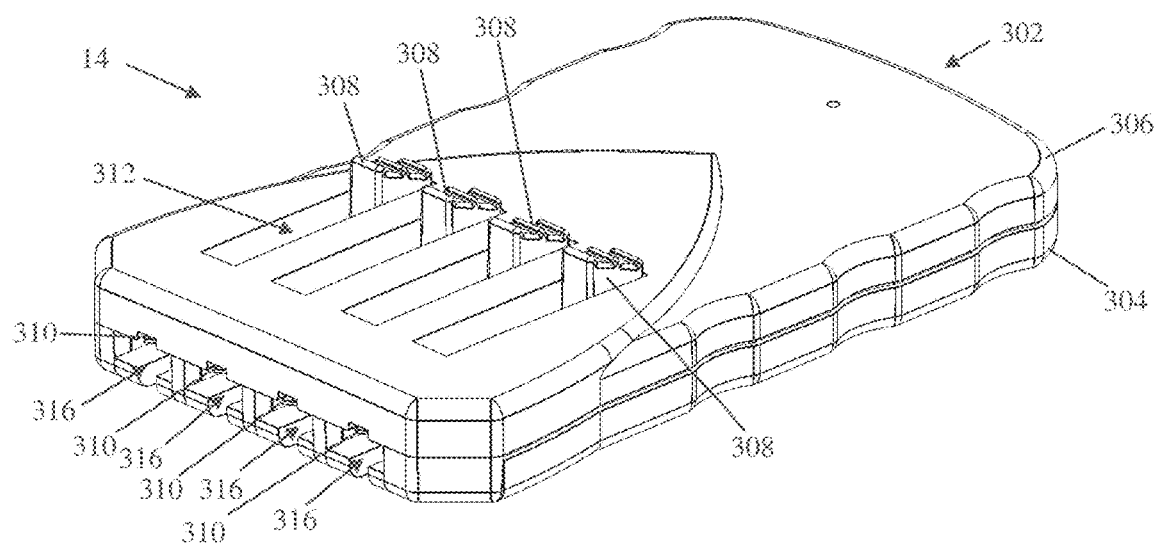
FIG. 2 is a perspective view of one example of the safety blade-dispenser of FIG. 1.
Figure 3:
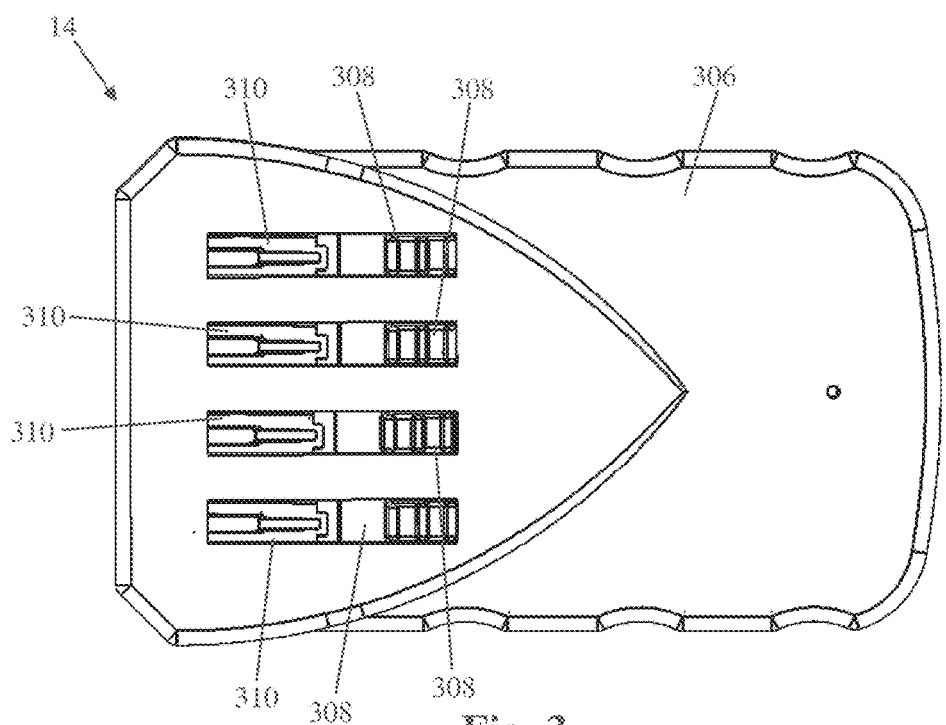
FIG. 3 is a top plan view of the safety blade-dispenser of FIG. 2.
Figure 4:
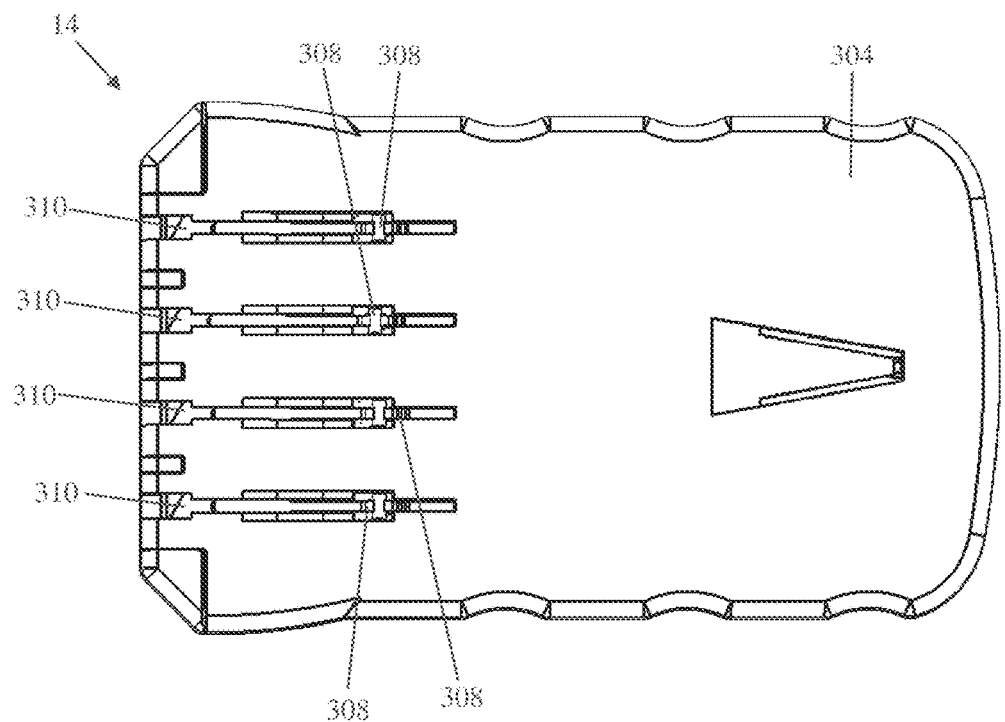
FIG. 4 is a bottom plan view of the safety blade-dispenser of FIG. 2.
Figure 5:
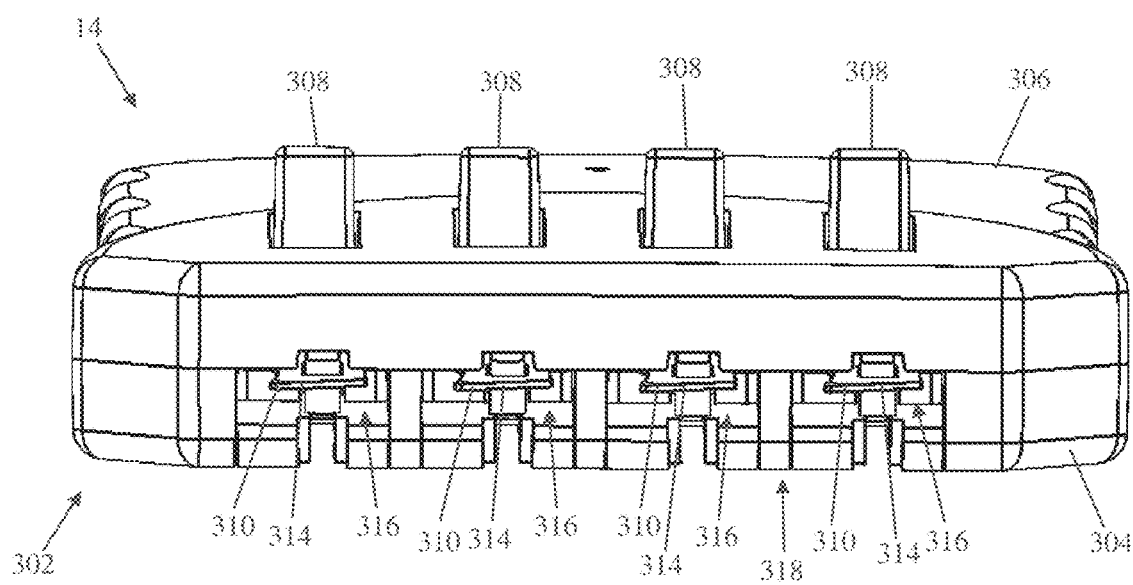
FIG. 5 is a front perspective view of the safety blade-dispenser of FIG. 2.
Figure 6:
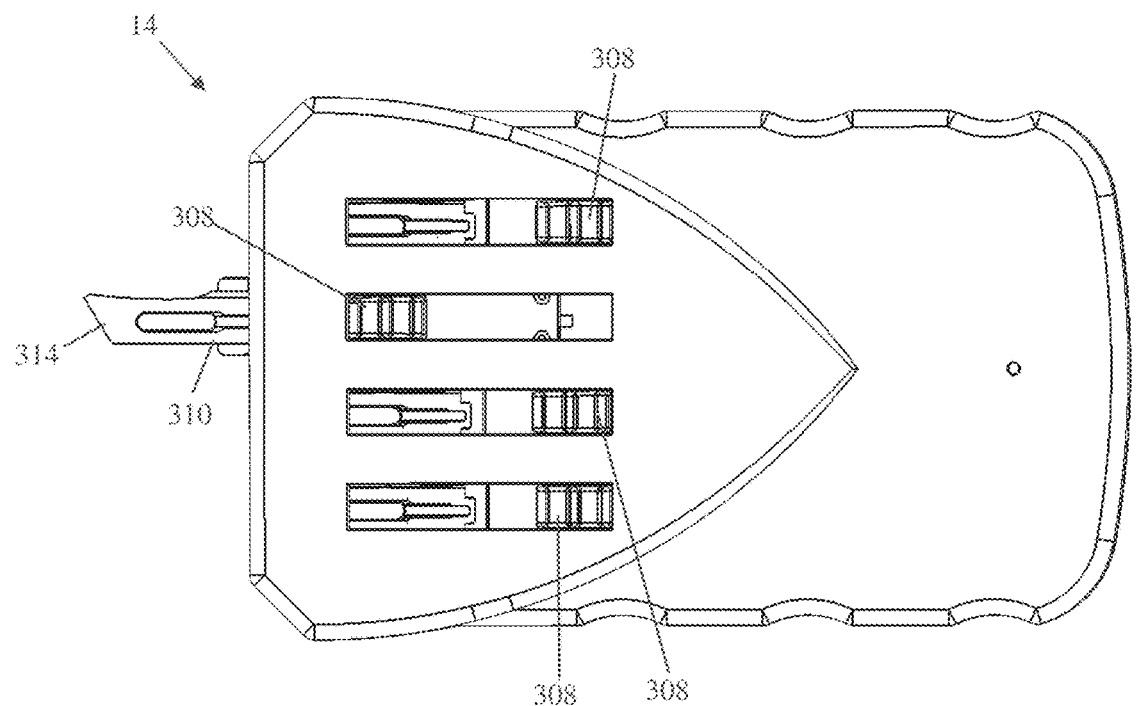
FIG. 6 is a top plan view of the safety blade-dispenser of FIG. 2 with one blade advanced to a removable position.
Figure 7:
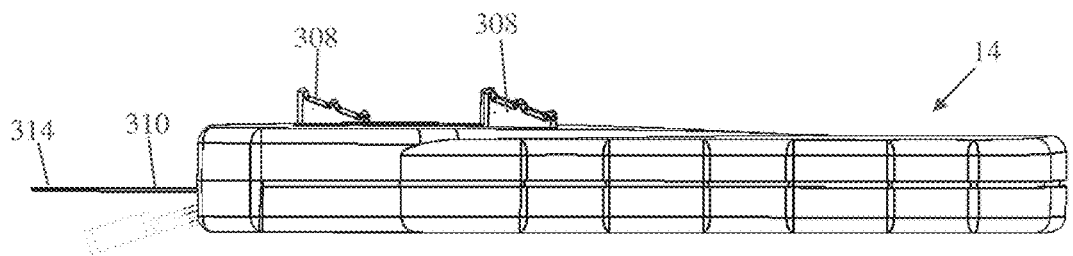
FIG. 7 is a side plan view of the safety blade-dispenser of FIG. 6.
Figure 8:
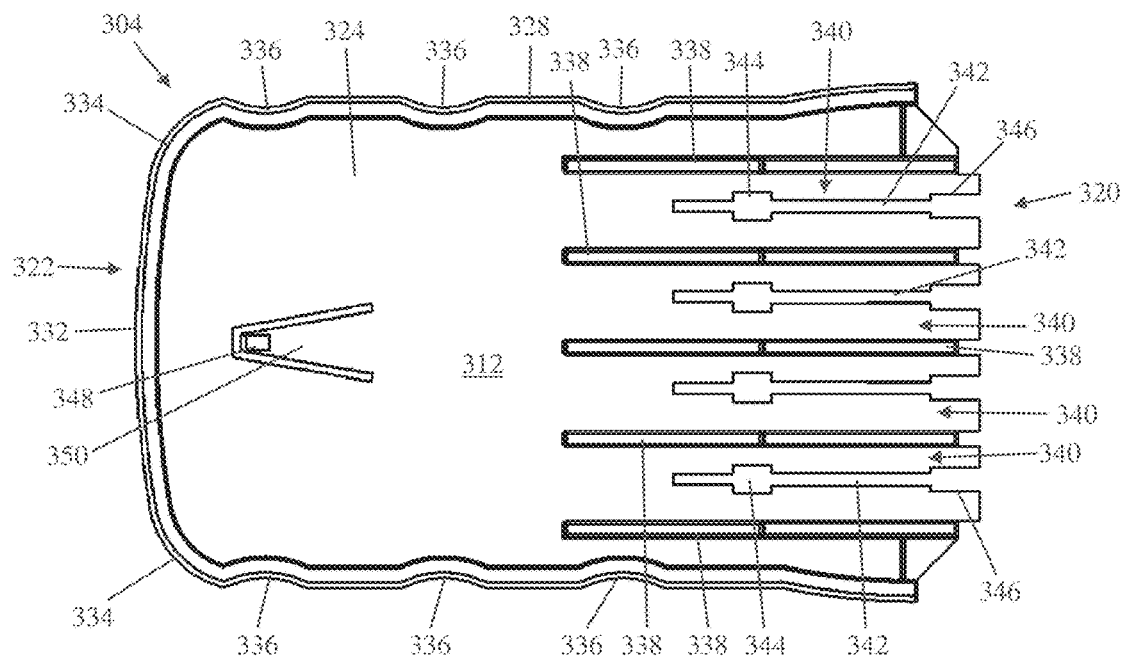
FIG. 8 is a plan view of a first housing panel forming part of the safety blade-dispenser of FIG. 2.
Figure 9:
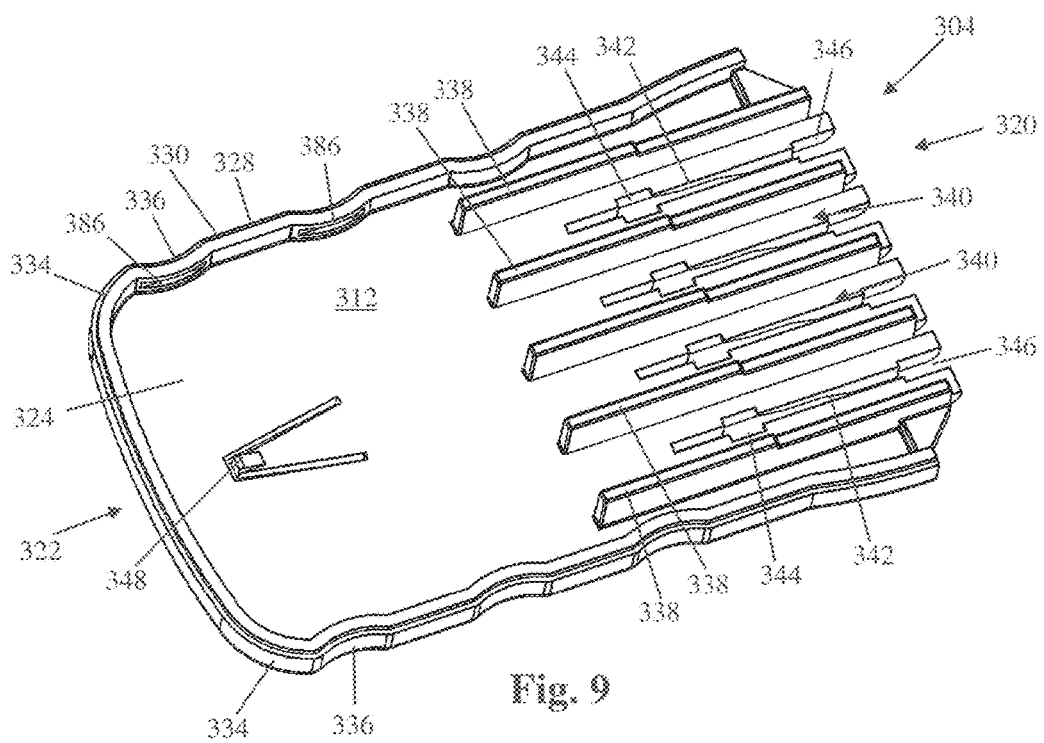
FIG. 9 is a perspective view of the first housing panel of FIG. 8.

While the present invention is susceptible of embodiment in various forms, there is shown in the drawings and will hereinafter be described a presently preferred, albeit not limiting, embodiment with the understanding that the present disclosure is to be considered an exemplification of the present invention and is not intended to limit the invention to the specific embodiments illustrated.

FIG. 1 is a graphical representation of an exemplary wrong-site surgery prevention system which may include any of the various safety-blade dispensers of the present disclosure for preventing or reducing blade-related injuries to OR personnel. As shown in the example embodiment of FIG. 1, a system 10 includes computer software system 12 configured to provide a user with a method of preventing wrong site surgeries, in combination with a safety blade-dispenser 14, as shown and described in the '210 PCT incorporated into this disclosure above. The safety blade dispenser 14 comprises at least one component, such as a label, paper, or tape, which prevents or impedes a surgeon from accessing one or more surgical instruments stored within until after a "time-out" is performed by the surgeon or authorized OR personnel before starting the intended surgical procedure. The computer software system 12 can be run on any of a variety of computing devices, such as a computer 16 (e.g. stationary desktop and/or laptop) and/or a hand-held computing device 18 (e.g. smart-phones such as IPHONE and/or a tablet device such as an IPAD or SURFACE PRO) used within the medical environment. The "medical environment" includes anywhere along the continuum in which patient and medical team (including the doctor, office personnel, nurses, medical technicians, surgeons, administrators) interact, from the surgeon's office (where the initial consultation and decision for surgery is made) to the operating room (where the surgery takes place). The term may also include personnel involved with post-surgical data collection and/or analysis, such as (but not limited to) (a) insurance companies for the patient, hospital and/or surgeon, (b) state and/or federal agency departments/programs (e.g. Medicare/Medicaid) which reimburse funds to the hospital and/or surgeon, (c) any other agency (private and/or governmental) which generates payment to the patient, hospital and/or surgeon for the specific surgical case, and/or (d) quality control and/or hospital administration to identify areas of improvement and/or best practices. The system and related methods of preventing wrong-site surgeries and sharps or blade-related injuries utilize computer software system 12 to support and provide several functionalities. These include, but are not necessarily limited to, voice recording 42, recording playback 44, an electronic patient-identifying component (such as a patient ID band 46) capable of being scanned, safety blade-dispenser 14 capable of being scanned, and any of a variety of analytics 48 generated or based upon data acquired through the use of the system 10 from "decision-to-incision", that is, from the decision to have surgery (made in the surgeon's office) through the actual surgery (in the OR). Scanning of the patient ID band 46 and/or safety blade-dispenser 14 may be accomplished by scanning functionality of the computer 16, hand-held device 18 and/or scanning systems separate from the system 10 which cooperate and communicate with the system 10. The system 10 may use any of a variety of suitable biometric identification technologies (e.g. iris scan, finger-prints, genetics, etc . . . ) in order to identify the patient (and/or the guardian of the patient if the patient is a minor or incapacitated) at any point in the medical environment.

FIGS. 2-22 illustrate a specific example of the safety-blade dispenser 14 suitable for use with the system and methods of preventing wrong-site surgeries and blade-related injuries 10 in a surgical procedure, although it is also possible that the safety blade-dispenser 14 may be used independently of the system and methods of preventing wrong-site surgeries and blade-related injuries 10. The safety blade-dispenser 14 described herein provides a compact and convenient vessel for storage and delivery of a variety of surgical sharps, including but not limited to surgical blades (shown by way of example herein throughout), scalpels, needles, probes, syringes, and the like. As will be described below, the safety blade-dispenser 14 may be provided with a removable confirmation label and/or additional features to help reduce the incidence of wrong site surgeries. Generally, the safety blade-dispenser 14 described herein by way of example comprises a generally rectangular container having a storage portion and a handle portion, the storage portion including four blade holders arranged side-by-side in a 1×4 matrix configuration. The blade holders are slideable in the same direction such that all four surgical blades are removed on the same side of the device. Although shown and described in relation to this example embodiment, other box shapes and/or configurations of surgical blades are possible without departing from the scope of this disclosure.

Referring to FIGS. 2-7, the safety blade-dispenser 14 of the present example includes a housing 302 comprising a first housing panel 304 and a second housing panel 306 and at least one blade holder assembly 308 configured to releasably hold a surgical blade 310. The first housing panel 304 and the second housing panel 306 mate to form the completed housing 302. Preferably, the safety blade-dispenser 14 includes a plurality of blade holder assemblies 308. By way of example only, the safety blade-dispenser 14 described herein includes four blade holder assemblies 308, however any number of blade holder assemblies 308 is possible. The blade holder assemblies 308 are moveable between a first position in which the surgical blade 310 is fully contained within the housing 302 (e.g. FIGS. 2-5) and a final position in which at least a portion of the surgical blade 310 is protruding from the housing 302 (e.g. FIGS. 6-7) to enable removal of the surgical blade 310 from the housing 302. By way of example, the movement may be unidirectional or bidirectional.

The housing 302 is generally compact in size, allowing the safety blade-dispenser 14 to be held and operated in the palm of a single user's hand, while being large enough to contain and dispense at least one surgical blade 310. The housing 302 is generally rectangular in shape with rounded and/or scalloped edges 336 for ease of gripping. The housing 302 may be made of plastic or any other suitable material. The housing 302 further has an interior cavity 312, see FIG. 9, flanked by the first and second housing panels 304, 306, in which the blade holder assemblies 308 and surgical blades 310 reside. The blades 310 emerge from the interior cavity 312 through distal openings 316 (e.g., apertures) formed within the distal end 318 of the housing 302, with the proximal end 314 of the blade 310 being presented for association with a suitable receiver (e.g. scalpel handle). Once the blade 310 has been attached to the receiver, it may be fully removed from the blade holder assembly 308 and used in the surgical procedure.

FIGS. 8-11 illustrate the first housing panel 304 in greater detail. The first housing panel 304 comprises a generally planar, generally rectangular member having a first end or distal end 320, a second opposing or proximal end 322, an interior surface 324 and an exterior surface 326. The interior surface 324 faces the interior cavity 312 when the first housing panel 304 is mated to the second housing panel 306 to form the housing 302. The interior surface 324 is generally smooth and generally planar and is flanked by a peripheral ridge 328 that forms a portion of the sidewalls 330 of the housing 302. The peripheral ridge 328 may have several ergonomic features that enable a user to comfortably and securely grip and operate the safety blade-dispenser 14 in a single hand, including but not limited to a curved proximal edge 332, rounded proximal corners 334, and a plurality of scalloped indentations 336. The curved proximal edge 332 and rounded proximal corners 334 enable a smooth feel in a user's hand while the scalloped indentations 336 provide extra grip for a user's fingers.

A plurality of parallel, elongated walls 338 extend longitudinally inward from the distal end 320 toward the proximal end 322. The space between two elongated walls 338 forms a channel 340 that is sized and configured to slideably receive one blade holder assembly 308 therein. Therefore, the number of elongated walls 338 provided depends upon the number and/or type of surgical blades 310 (or other surgical sharps) a particular safety blade-dispenser 14 contains. In the instant example, the first housing panel 304 includes five elongated walls 338 spaced apart to form four channels 340 to receive the four blade holder assemblies 308 therein. Each channel 340 further includes an elongated slit 342 formed through the first housing panel 304 between the interior and exterior surfaces 324, 326 and extending inward from the distal end 320. As will be described in further detail below, the elongated slit 342 enables controlled translation of the blade holder assembly 308 within the channel 340. The elongated slit 342 is configured to slideably receive the post 420 of the blade holder assembly 308 therethrough. Each elongated slit 342 further includes a first, or proximal widening 344 and a second, or distal widening 346. The proximal widening 344 allows passage of the crossbar 422 of the blade holder assembly 308 through the first housing panel 304 during assembly and is shown by way of example as a generally rectangular aperture. The distal widening 346 allows the shaped end 418 of the blade holder assembly 308 to pass through the first housing panel 304 while it pivots away from the surgical blade 310 (and out of the central aperture 428) to enable removal of the surgical blade 310 once the blade holder assembly 308 is fully translated. By way of example, the distal widening 346 comprises a generally rectangular cutaway having one edge at the proximal end 320.

The first housing panel 304 further includes a lock tab 348 configured to prevent the first housing panel 304 from dissociating from the second housing panel 306 absent a sufficient targeted force. The lock tab 348 comprises a flange 350 that is biased inward (e.g. into the interior cavity 312 of the housing 302). When the housing 302 is properly assembled, the lock tab 348 abuts the lock post 380 of the second housing panel 306 (see FIG. 12), preventing dissociation of the first and second housing panels 304, 306. To unlock the safety blade-dispenser 14, a user inserts a suitable unlocking tool through the proximal unlock aperture 378 of the second housing panel 306 so that the unlocking tool engages the lock tab 348. The user then exerts a sufficient force to cause the lock tab 348 to pivot against the inward bias and lift over the lock post 380, enabling the first and second housing panels 304, 306 to be dissociated from one another. This might be necessary for example if the user wanted to load different set of surgical blades 310 before beginning the surgical procedure.

Figure 10:
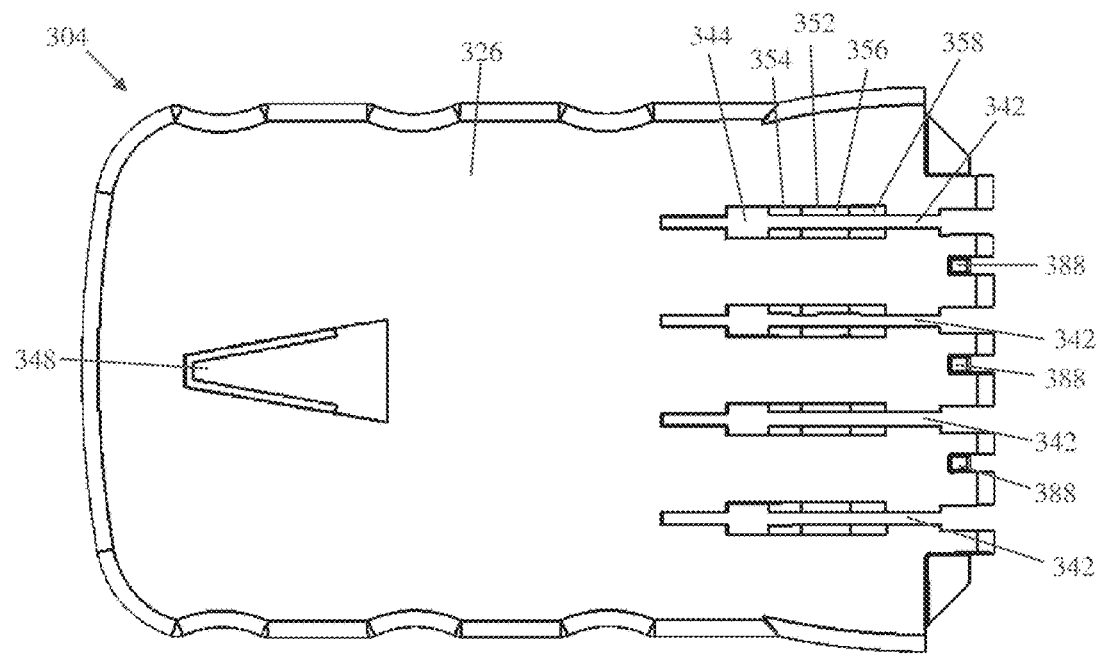
FIG. 10 is another plan view of the first housing panel of FIG. 8.
Figure 11:
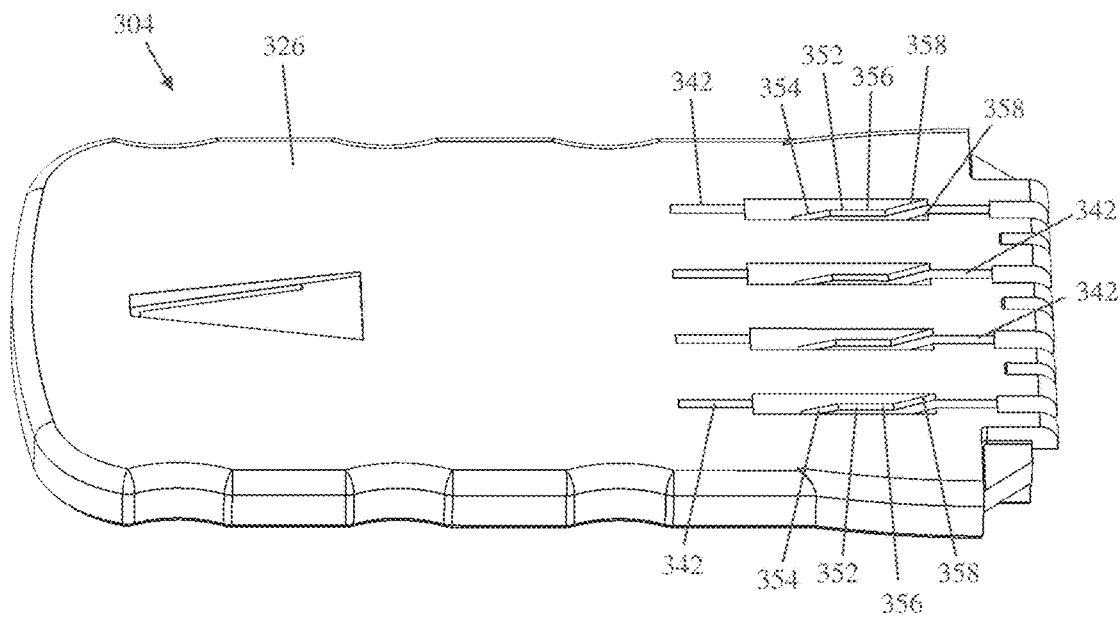
FIG. 11 is another perspective view of the first housing panel of FIG. 8.

Referring now to FIGS. 10-11, the exterior surface 326 faces away from the interior cavity 312 when the first housing panel 304 is mated to the second housing panel 306 to form the housing 302, and is the surface that interacts with a user's hand. As such, the exterior surface 326 may be provided with one or more frictional elements to improve a user's grip on the device. The exterior surface 326 further includes a pair of ramped ledges 352 flanking each elongated slit 342. Each ramped ledge 352 includes a first beveled portion 354, a generally level intermediate portion 356, and a second beveled portion 358. The first beveled portion 354 is positioned adjacent the proximal widening 344 and includes the thinnest portion of the ramped ledge 352. The intermediate portion 356 is generally level (e.g. generally parallel to the exterior surface 326). The second beveled portion 358 is positioned adjacent the intermediate portion 356 and includes the thickest portion of the ramped ledge 352. As will be explained in further detail below, the ramped ledges 352 interact with the blade holder assembly 308 to release the surgical blade 310 from the holder assembly 308, thereby making the blade 310 available for interaction with an appropriate receiver (e.g. scalpel handle).

Figure 12:
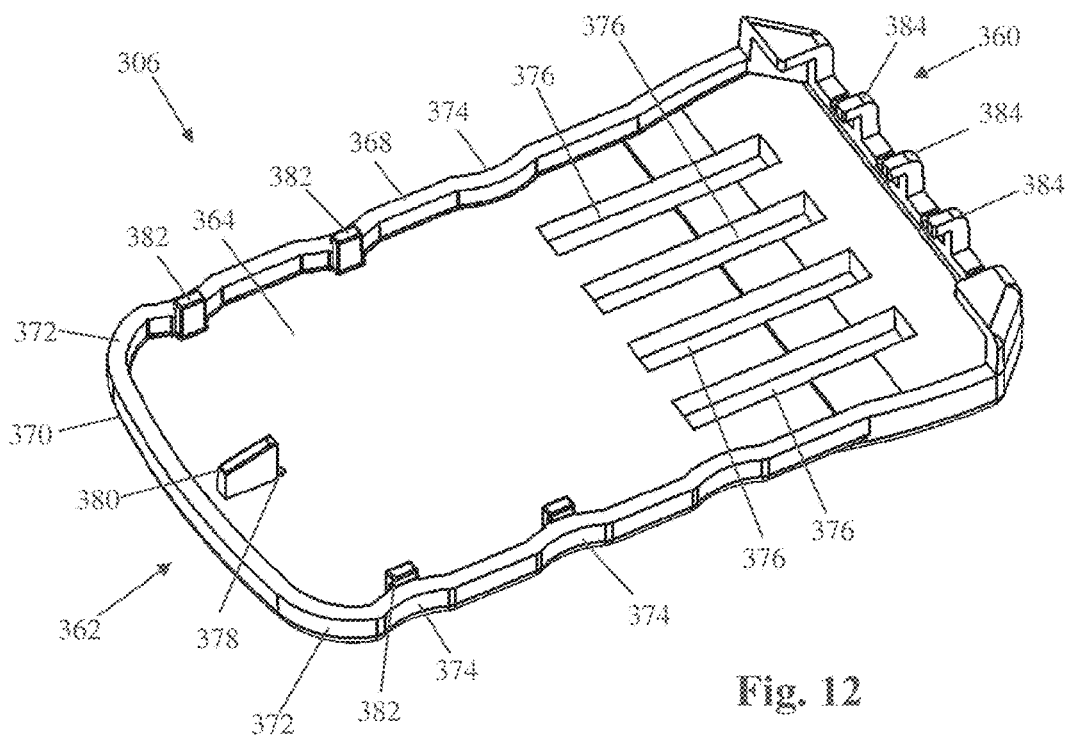
FIG. 12 is a perspective view of a second housing panel forming part of the safety blade-dispenser of FIG. 2.
Figure 13:
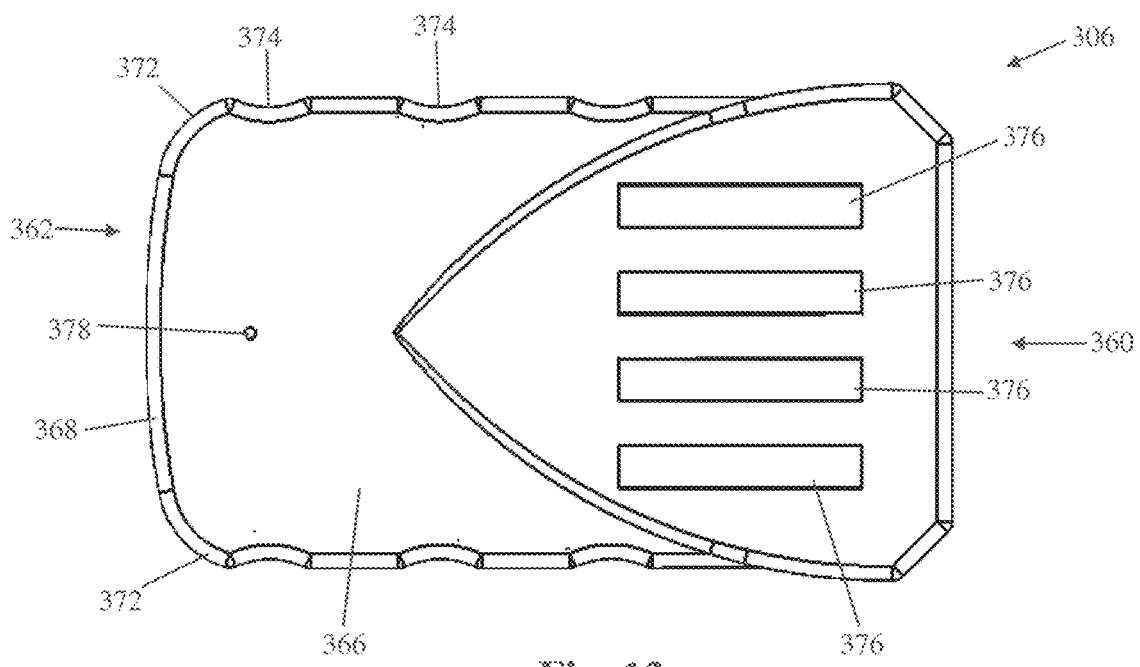
FIG. 13 is a plan view of the second housing panel of FIG. 12.

FIGS. 12-13 illustrate the second housing panel 306 in greater detail. The second housing panel 306 comprises a generally planar, generally rectangular member having a first or distal end 360, a second opposing or proximal end 362, an interior surface 364 and an exterior surface 366. The interior surface 364 faces the interior cavity 312 when the second housing panel 306 is mated to the first housing panel 304 to form the housing 302. The interior surface 364 is generally smooth and generally planar and is flanked by a peripheral ridge 368 that forms a portion of the sidewalls 330 of the housing 302. The peripheral ridge 368 may have several ergonomic features that enable a user to comfortably and securely grip and operate the surgical sharp dispenser 300 in a single hand, including but not limited to a curved proximal edge 370, rounded proximal corners 372, and a plurality of scalloped indentations 374. The curved proximal edge 370 and rounded proximal corners 372 enable a smooth feel in a user's hand while the scalloped indentations 374 provide extra grip for a user's fingers.

The second housing panel 306 further includes a plurality of elongated openings 376 positioned near the distal end 360. The elongated openings 376 not only function to allow passage of the engagement flange 396 of the blade holder assembly 308 through the second housing panel 306, but also provide a visible window through which a user can see the surgical blades 310 contained therein. The proximal unlock aperture 378 is positioned near the proximal end 362 and allows a user to unlock the safety blade-dispenser 14 if so desired. The lock post 380 is positioned near the proximal end 362 and extends from the interior surface 364. As explained previously, the lock post 380 interacts with the lock tab 348 to prevent the housing 302 from coming apart until desired by the user. Proximal coupling flanges 382 and distal coupling flanges 384 are configured to engage the proximal coupling apertures 386 and the distal coupling apertures 388, respectively, on the first housing panel 304 to hold the housing 302 together.

Figure 14:
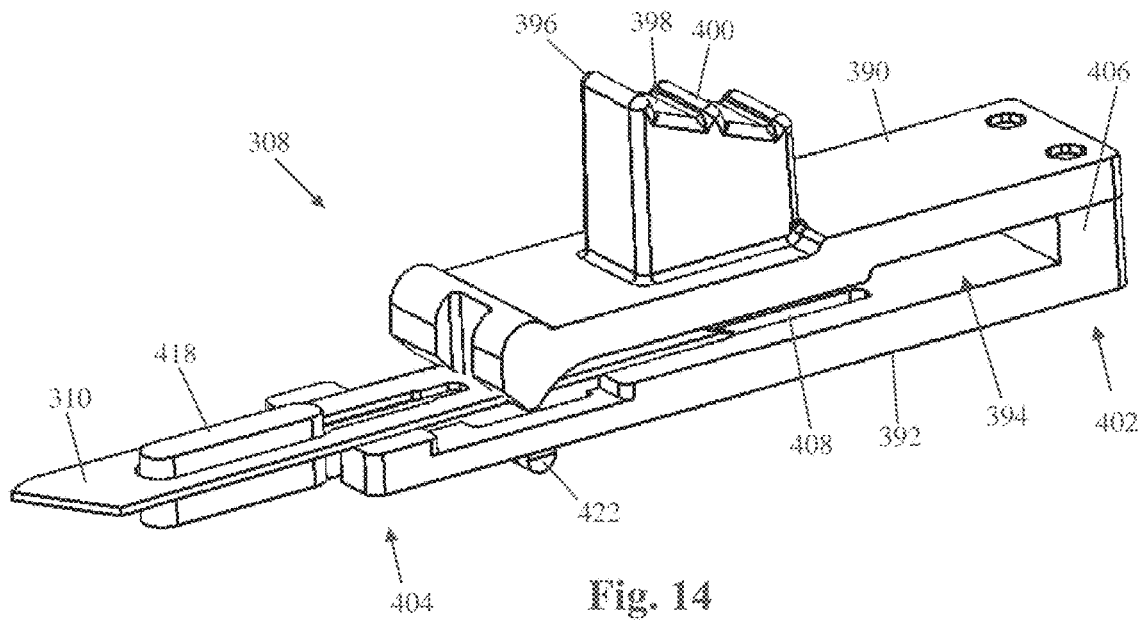
FIG. 14 is a perspective view of a blade holder assembly forming part of the safety blade-dispenser of FIG. 2.
Figure 15:
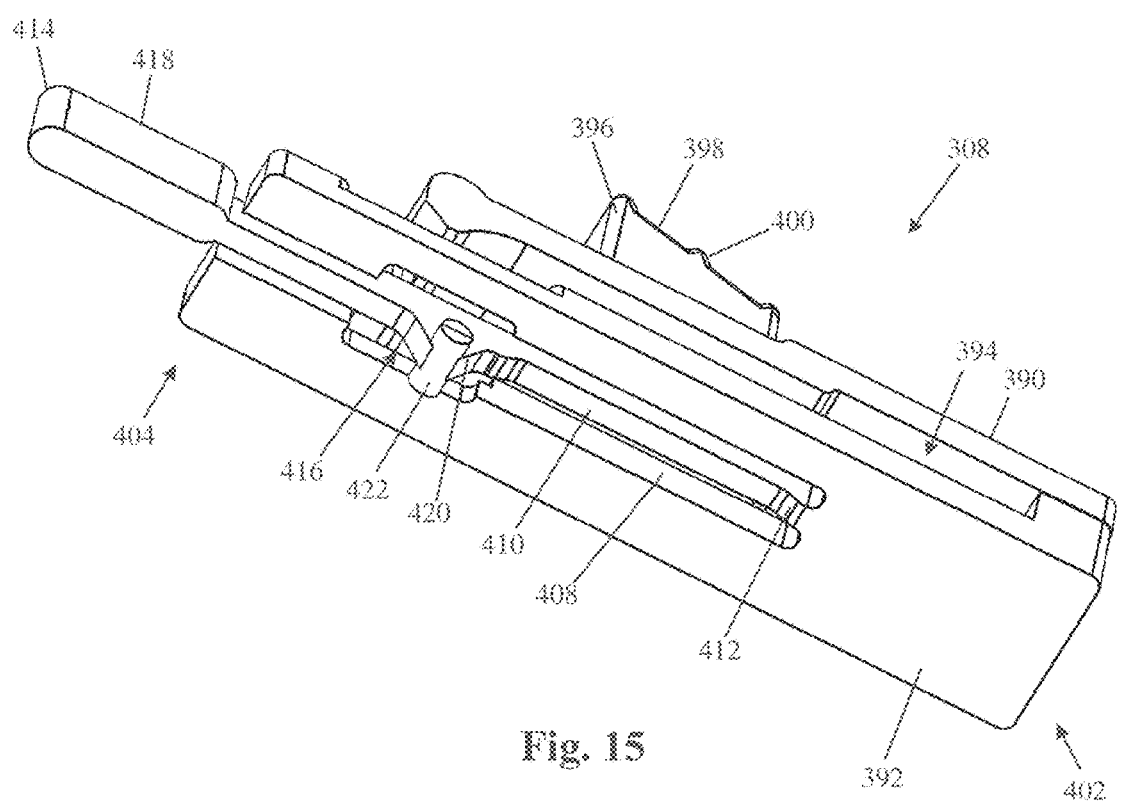
FIG. 15 is another perspective view of the blade holder assembly of FIG. 14.
Figure 16:
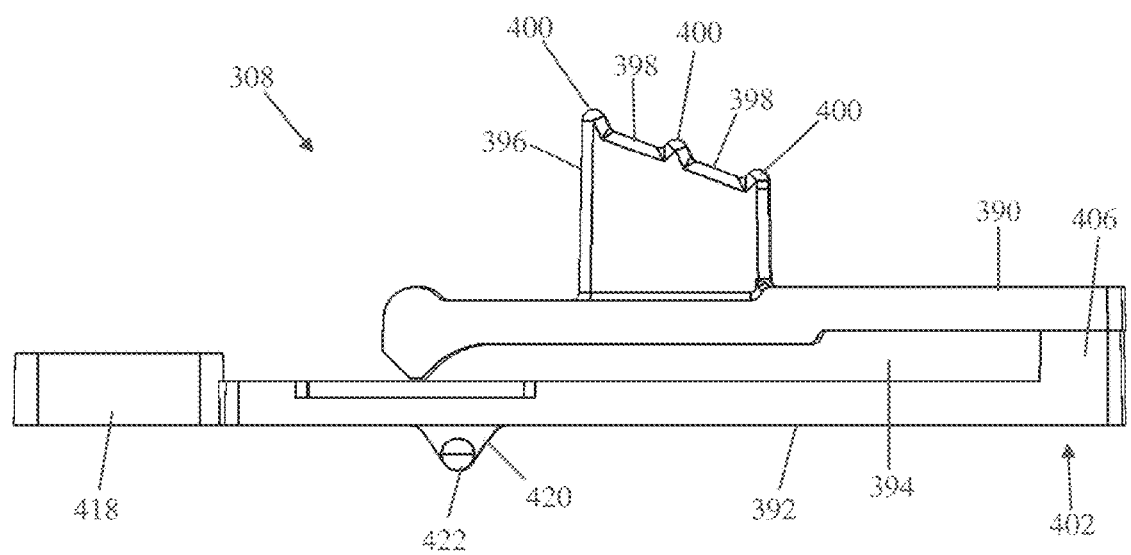
FIG. 16 is a side plan view of the blade holder assembly of FIG. 14.

FIGS. 14-16 illustrate one example of a surgical blade holder assembly 308 in greater detail. The surgical blade holder assembly 308 described herein includes a top panel 390 connected to a bottom panel 392 in such a way that creates a space 394 in between the top and bottom panels 390, 392. The top panel 390 includes an engagement flange 396 extending generally perpendicularly away from the top panel 390. The engagement flange 396 extends through an elongated opening 376 of the second housing panel 306 and includes an angled top surface 398 that may include one or more friction elements 400 (e.g. ridges) to improve the ability of a user to move the blade holder assembly 308 during use.

The bottom panel 392 by way of example has a generally rectangular shape, and includes a first or proximal end 402 and a second or distal end 404. The proximal end 402 includes an attachment post 406 extending from the upper surface of the bottom panel 392, to which the top panel 390 is attached thus creating the space 394. The bottom panel 392 further includes an elongated recess 408 formed therein and extending from the distal end 404 into the interior of the bottom panel 392. An elongated flange 410 having a proximal end 412, a distal end 414, and an intermediate portion 416 extends proximally back through the elongated recess 408. The proximal end 412 of the elongated flange 410 is attached to (or may be an integral extension of) the bottom panel 392. The distal end 414 of the elongated flange 410 includes a shaped end 418 sized and configured to securely engage the central aperture 428 of the surgical blade 310. The shaped end 418 extends beyond the distal end 404 of the bottom panel 392. The intermediate portion 416 includes a post 420 having a crossbar 422 positioned at the end of the post 420. The post 420 is sized to extend through and translate within the elongated slit 342 of the first housing panel 304.

The crossbar 422 interacts with the ramped ledges 352 flanking each elongated slit 342 as the blade holder assembly 308 is translated during use. More specifically, as the blade holder assembly 308 is translated distally along the channel 340, the crossbar 422 first engages the first beveled portions 354 of the ramped ledges 352. This initial interaction provides some physical resistance to the translational movement of the blade holder assembly 308 and helps prevent unintentional ejection of the surgical blades 310. That is, in order to overcome the physical resistance to translation, the user must apply a greater force to the engagement flange 396. Once the crossbar 422 reaches the intermediate portions 356, the proximal end 314 of the surgical blade 310 starts to emerge from the corresponding distal opening 316. At this point the user may view a size marking on the proximal end 314 of the blade 310 to confirm it is the intended surgical blade 310. Additional force is needed to traverse the second beveled portion 358 as it is beveled at a greater angle than the first beveled portion 354. This interaction forces the elongated flange 410 to temporarily bend, which urges the shaped end 418 out of the central aperture 428 of the surgical blade 310 (e.g. FIG. 7), allowing the surgical blade 310 to be engaged with another instrument (e.g. scalpel handle) and removed from the safety blade-dispenser 14.

Figure 17:
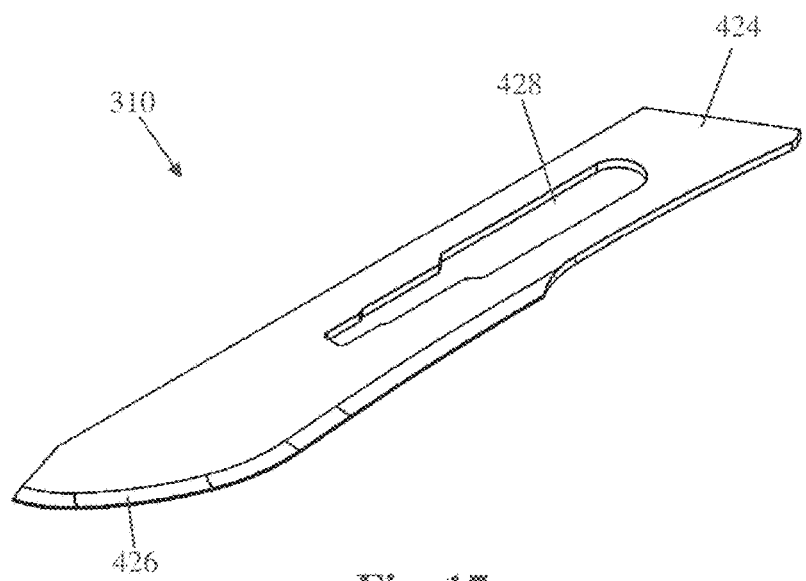
FIG. 17 is a perspective view of an example of a surgical blade configured for use with the safety blade-dispenser of FIG. 2.

FIG. 17 illustrates one example of a surgical blade 310 suitable for use with the safety blade-dispenser 14 of the present disclosure. By way of example, the surgical blade 310 includes an engagement portion 424 and a blade 426. The engagement portion 424 includes a central aperture 428 having a size and shape that is complementary to the shaped end 418 so as to securely receive the shaped end 418 therein.

Figure 18:
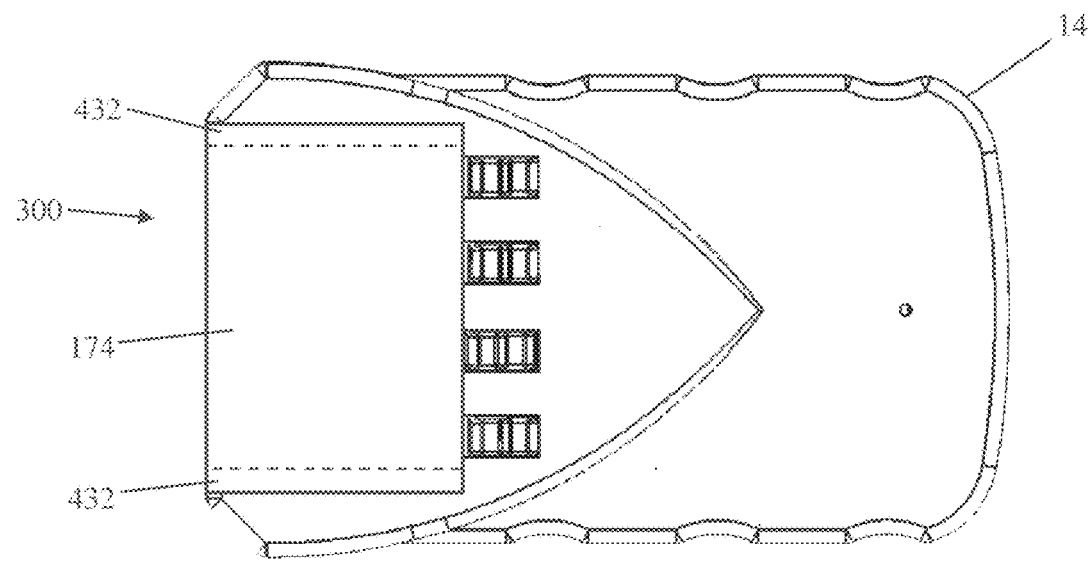
FIGS. 18 and 19 are plan views of the safety blade-dispenser of FIG. 2 with a confirmation label attached.
Figure 19:
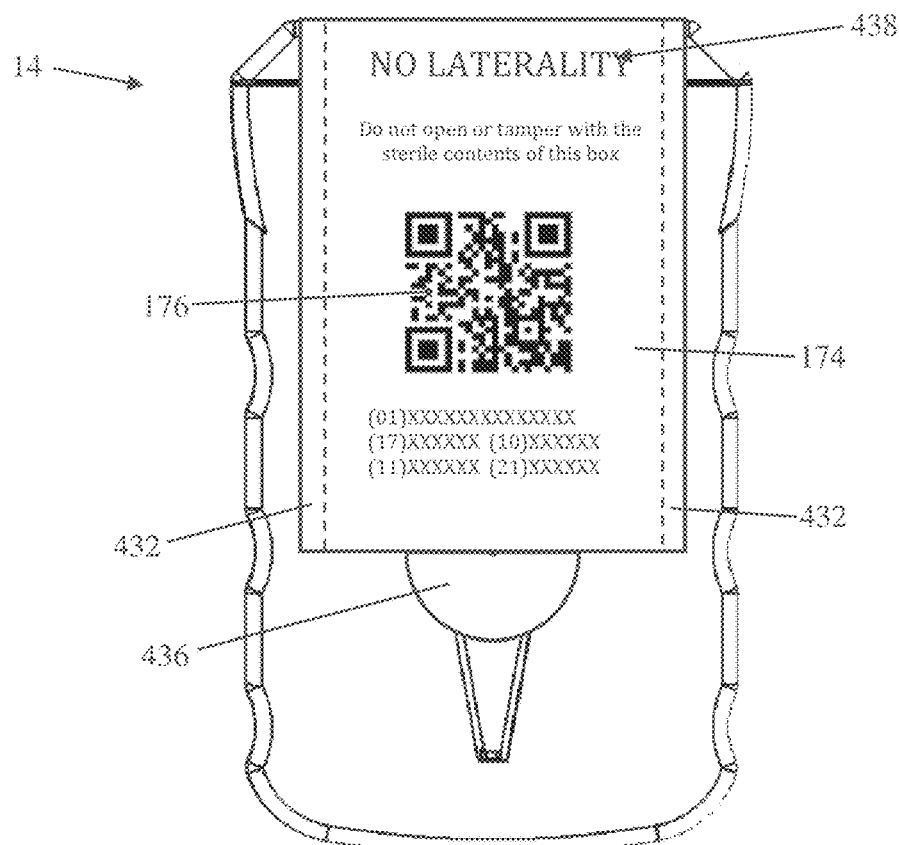

Referring to FIGS. 18-19, the safety blade-dispenser 14 shown and described herein may be provided with a confirmation label 174 to help reduce the prevalence of wrong site surgeries. The confirmation label 174 is placed in a manner that renders the surgical blades 310 inaccessible unless and until the user removes the label 174. The confirmation label 174 does not have adhesive on it, but is affixed to the safety blade-dispenser 14 via attached sticky strips 432 from which the label 174 can be torn away. By way of example, the confirmation label 174 may include any suitable patient data printed on the label and/or contained in an electronically scannable code (e.g. QR code 176, bar code, and the like) that the user must scan before removing the confirmation label 174. The confirmation label 174 further includes a pull-tab 436 to enable more efficient removal. In addition to patient data, the confirmation label 174 may include a laterality indicator 438 that immediately visually conveys to the user the laterality, if any, of the procedure. This laterality indicator 438 may include words and/or be color coded. For example, the label may include the words "LEFT" and/or be colored lavender to indicate a left side surgery, "RIGHT" and/or red color to indicate a right side surgery, and "NO LATERALITY" and/or gray color to indicate no laterality. Once the confirmation label 174 has been removed, it can be attached to the patient record by any suitable means.

Figure 20:
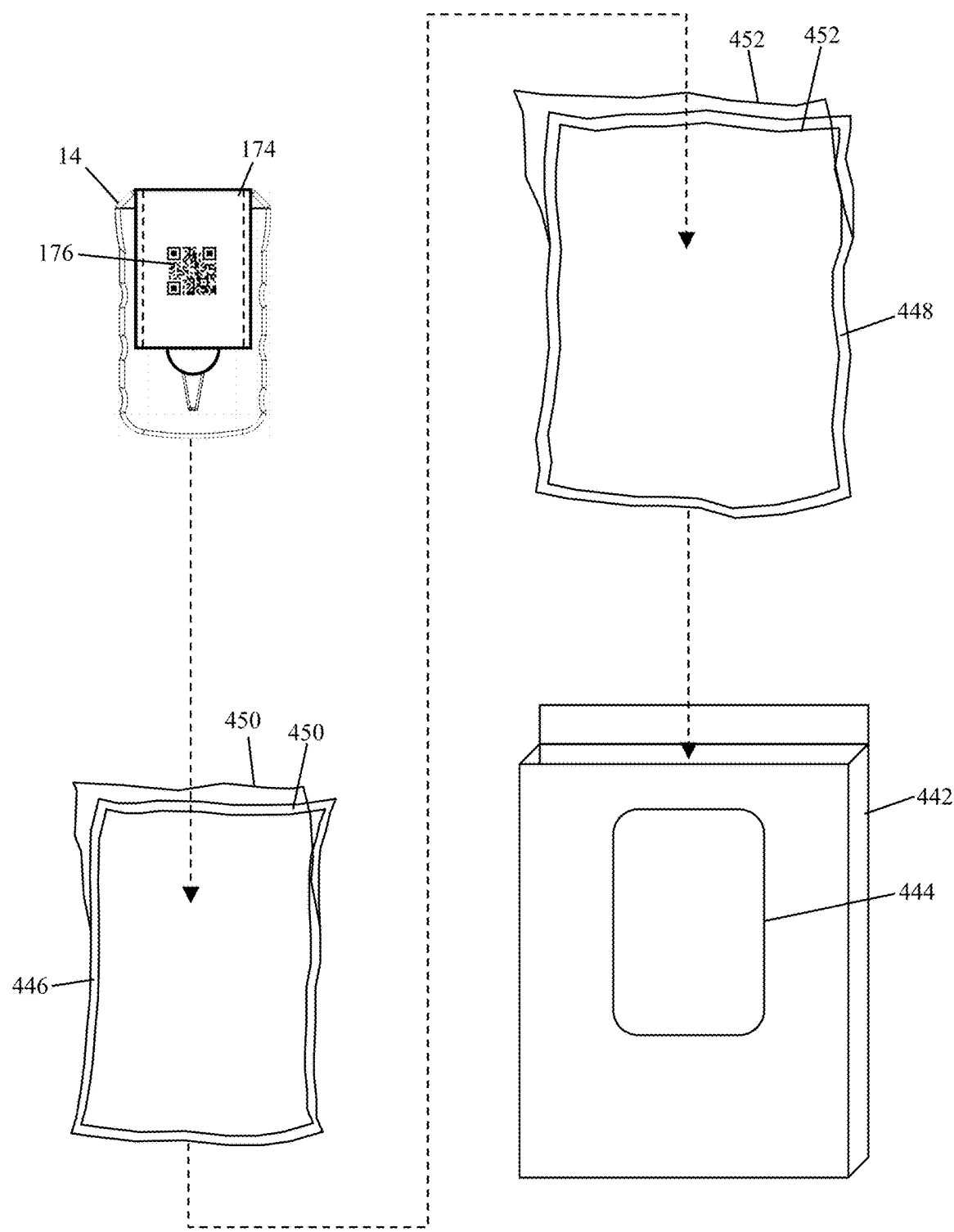
FIG. 20 is an exploded perspective view of the safety blade-dispenser of FIG. 2 with dual inner packaging (sterile and transparent) and an outer container with transparent viewing window according to an aspect of the present disclosure.
Figure 21:
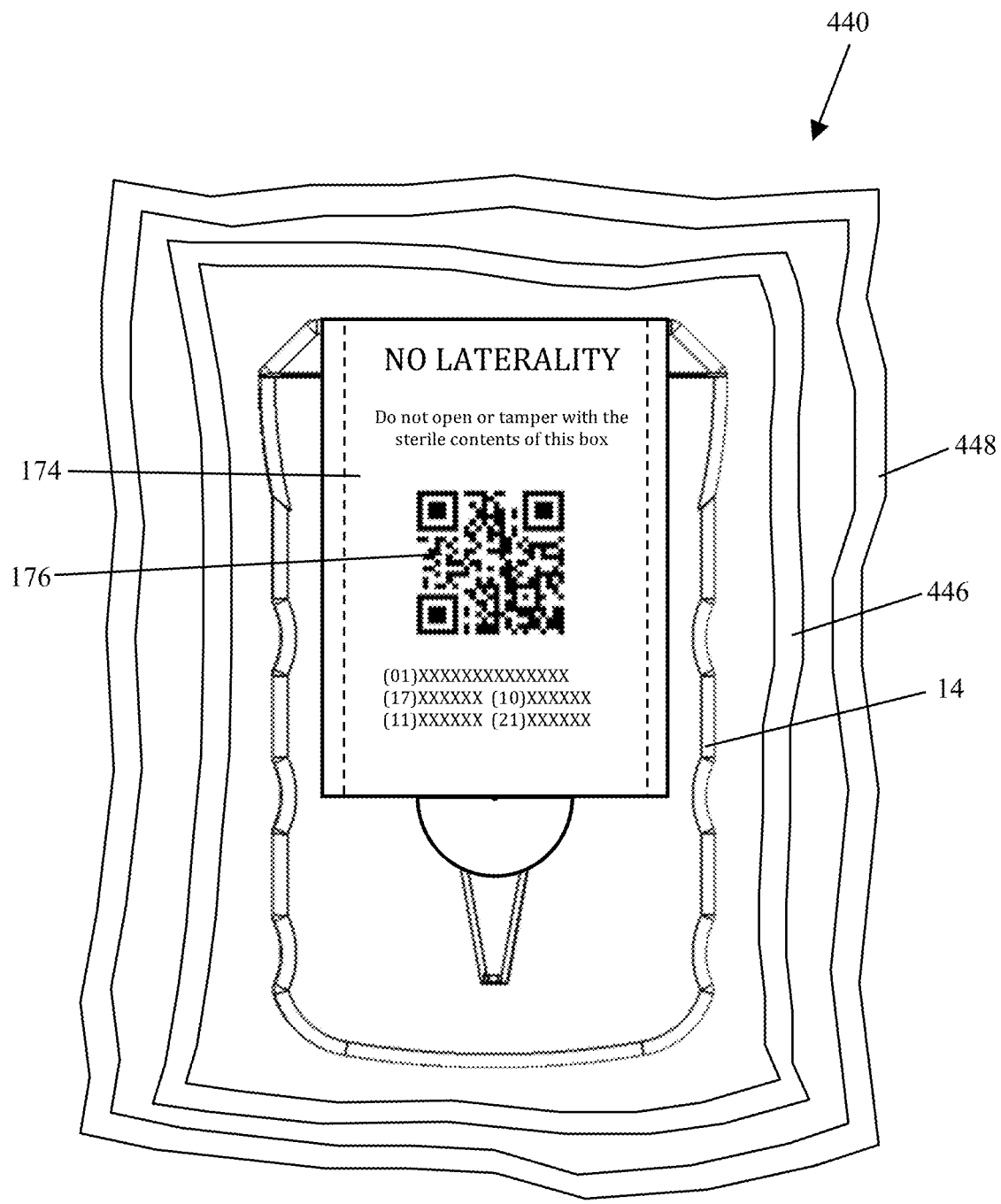
FIG. 21 is a plan view of the safety blade-dispenser of FIG. 20 sealed within the dual sterile and transparent inner packaging.
Figure 22:
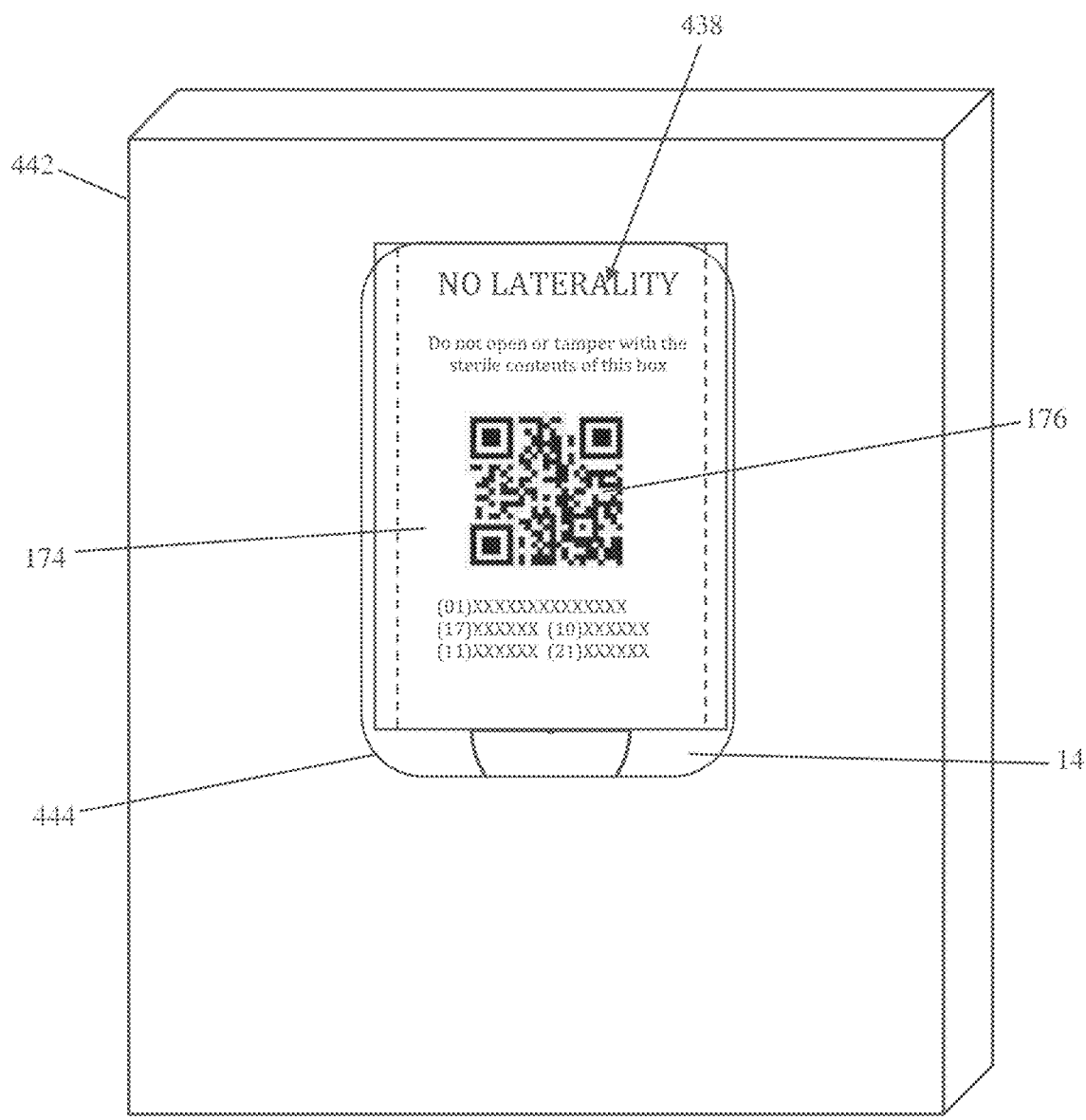
FIG. 22 is a perspective view of the safety blade-dispenser of FIG. 21 sealed within the dual sterile and transparent inner packaging and further enclosed within the outer container with transparent viewing window for viewing the label of the safety-blade dispenser while fully sealed and packaged.

As shown in FIGS. 20-22, the safety blade-dispenser 14 of the present disclosure is preferably provided within double sterile packaging 440 disposed within a container 442 having a transparent window section 444. More specifically, the safety blade-dispenser 14 is disposed within a first sterile package 446, which is then sealed within a second sterile package 448. Both the first and second sterile packages 446, 448 are transparent and relatively easy to open (using pull-apart flaps 450, 452 positioned on one end of each package 446, 448, respectively). The combined sterile packages 446, 448 are disposed within the container 442 such that identifying information on the confirmation label 174 (e.g. QR code 176 and/or laterality indicator 438) may be scanned through the transparent window section 444 of the container 442 and the transparent first and second sterile packages 446, 448. In this manner, one can avoid the need to have the same identifying information on any of the packaging (i.e. first sterile package 446, second sterile package 448, or outer container 442). This reduces manufacturing costs and the complexity of matching multiple packaging components to ensure they all have the same identifying information, which would otherwise be required but for the transparent sterile packages 446, 448 within the container 442 having the transparent window section 444 through which the identifying information on the label 174 may be scanned.

Although the safety blade-dispenser 14 is shown and described as having four blade holder assemblies 308 arranged side-by-side (e.g. 1×4 matrix), other configurations are possible. For example, a narrower container may be provided where the blades 310 are arranged in a planar 2×2 matrix configuration, where two blades 310 are ejected in one direction and the other two blades are ejected in the opposite direction. The planar configuration allows all four viewing apertures to be on the same side of the device for ease of counting the blades. Another possible configuration includes a stacked 2×2 matrix configuration, where all four blades 310 may be ejected in the same direction, but only two are visible at any one time. The user would have to rotate the container to view the other two blades. In another alternative example, a non-rectangular container may be provided wherein the blades 310 are ejected at a slight angle. Blade configuration in such a container may be 1×4, 2×2 or any other configuration that is safe for the user.

The blades 310 provided in the safety blade-dispenser 14 have been carefully selected in advance of the patient's surgery. Therefore, it is critical that the safety blade-dispenser 14 be in the physical vicinity of the patient at all times prior to the procedure. One such possibility is that the safety blade-dispenser 14 (as provided in FIGS. 21-22 in double sterile packaging 440 and outer container 442 with a confirmation label 174 clearly visible) is attached to the patient's medical chart in a non-obstructive manner. The attachment may be accomplished by any suitable method, for example including but not limited to elastic band, tape, binder clip (integrated or stand-alone), hook and loop fasteners (e.g. Velcro), suction cup, zip tie, hole for ring binder, and the like. Another possibility is to attach the safety blade-dispenser 14 directly to the patient, for example via a wristband or ankle band. Still another possible location may be to attach the safety blade-dispenser 14 to the patient's IV stand or drip bag.

Figure 23:
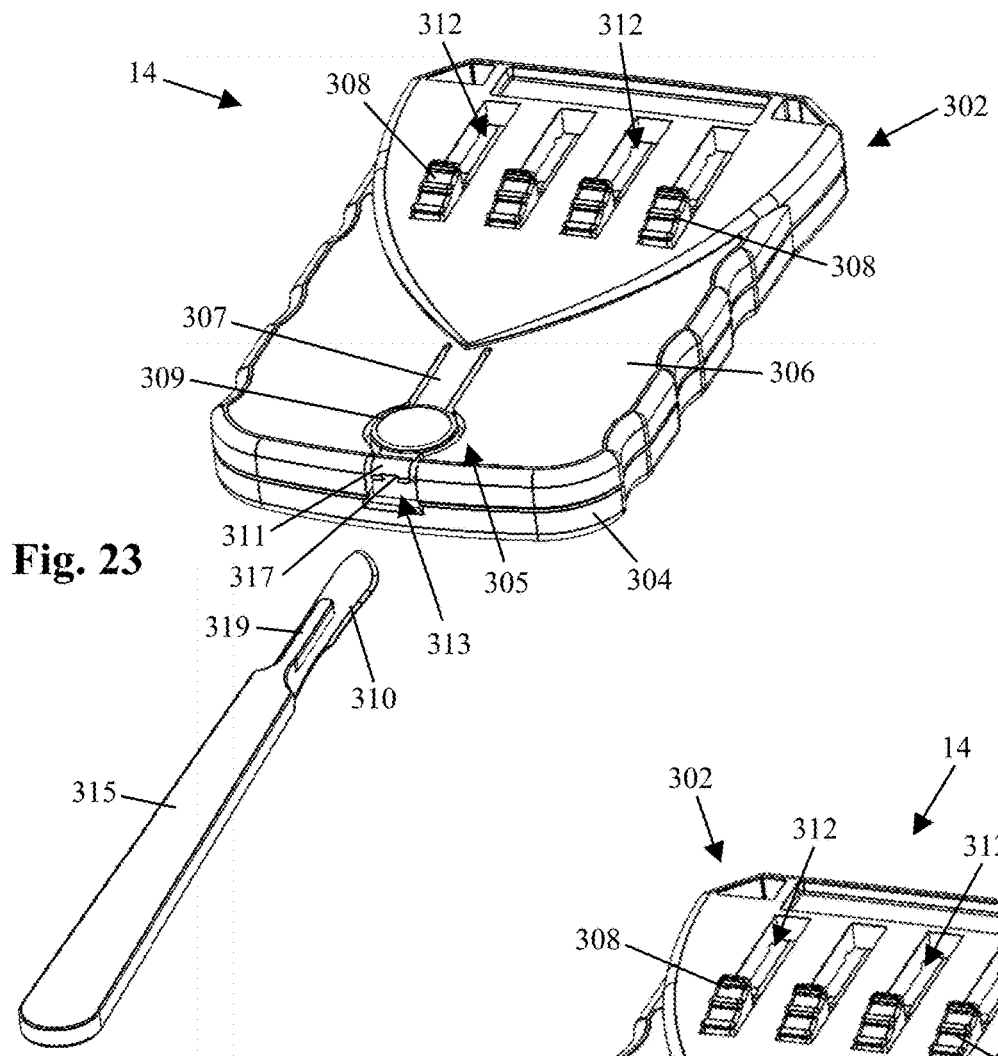
FIG. 23 is a safety-blade dispenser of the type shown in FIG. 2 with an optional blade removal feature, illustrating a blade and handle positioned to be inserted into a blade removal aperture.
Figure 24:
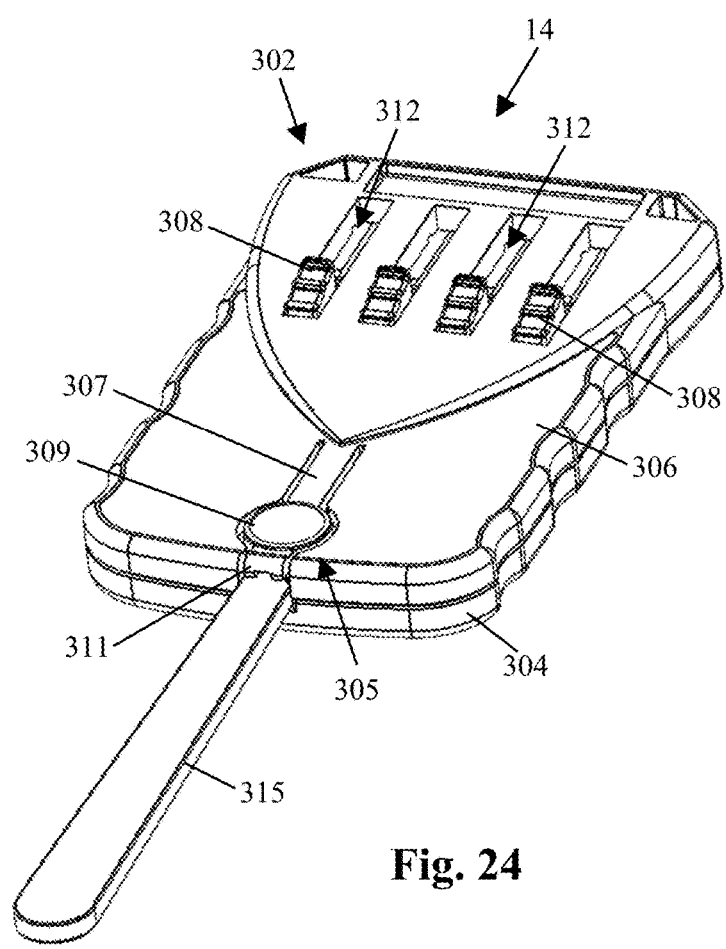
FIG. 24 is the safety-blade dispenser of FIG. 23 with the optional blade removal feature, illustrating the blade and handle positioned within the housing to remove the blade.

FIGS. 23 and 24 illustrate an optional blade removal feature that may be provided as part of the safety-blade dispenser 14 according to one aspect of the present disclosure. In particular, the housing 302 may be equipped with a flexible element 305 formed as an integral and contiguous part of the second housing member 306. The flexible element 305 includes an elongated first section 307, an expanded second section 309, and an end section 311. The elongated first section 307 extends rearwardly from a generally central region of the second housing member 306. The expanded second section 309 has an expanded or enlarged periphery relative to that of the elongated first section 307 and the end section 311. By way of example only, the expanded or enlarged periphery of the expanded second section 309 may take the form of a generally circular or disc-shape, although it will be appreciated that any number of suitable shapes may be employed without departing from the present disclosure. The end section 311 extends rearwardly from the expanded second section 309 and forms part of a boundary of blade removal aperture 313.

The blade removal aperture 313 extends into the interior cavity 312 of the housing 302 and is dimensioned to receive the surgical blade 310 and a distal region of a blade handle 315. More specifically, the interior surface of the end section 311 (and optionally the expanded second section 309) is equipped with an elongated recess or notch 317 that matches the approximate profile of a blade engagement arm 319 of the blade handle 315.

When a user wants to remove the surgical blade 310 from the blade handle 315, he or she can simply align the blade handle 315 and blade 310 with the longitudinal axis of the blade removal aperture 313 and then introduce the distal region of the scalpel (that is, the blade 310, the blade engagement arm 319, and a distal section of the blade handle 315 as shown in FIG. 24). At that point, the user may press down upon the expanded second section 309 of the flexible element 305 in order to pinch or otherwise retain the blade 310. With the blade 310 temporarily immobilized due to the compression of the expanded section 309 (such as by the user pressing their thumb against the expanded section 309 with one hand), the user may then tilt or otherwise angle the blade handle 315 to release the blade 310 from the blade engagement arm 319.

Once the blade 310 has been disengaged from the handle 315, the flexible element 305 may then be released such that the handle 315 may be removed from the blade removal aperture 313 while the blade 310 remains within the internal cavity 312 of the housing 302. In this manner, the user may safely remove the blade 310 after surgery without needing to physically touch or manipulate the blade with their hands, which represents an improved safety profile due to the reduction in blade related injuries due to blade handling. The internal cavity 312 may be dimensioned to house or retain one or multiple retrieved blades after use in surgery. The confirmation label 174 may be dimensioned to cover the blade retrieval aperture 313 prior to use of the blade dispenser 14 in surgery. After the removal of the blade(s), tape or any other suitable blocking mechanism may be employed to prevent the egress of any of the retrieved blades 310 that have been removed and stored within the housing 302, if required.

Figure 25:
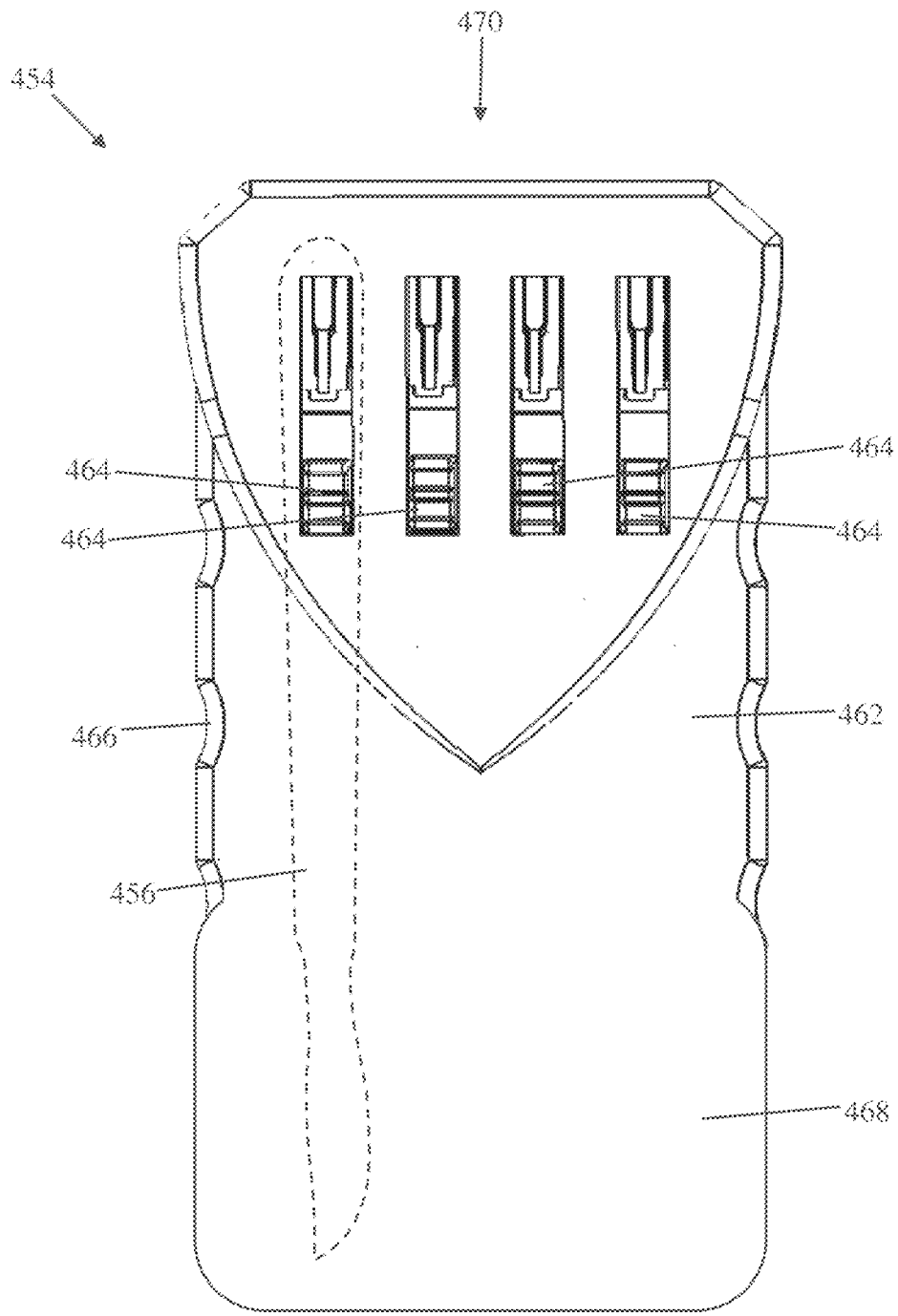
FIG. 25 is a plan view of an alternative example of a safety blade-dispenser of the type shown in FIG. 2 configured to hold an assembled or unitary scalpel (that is, blade and handle)
Figure 28:
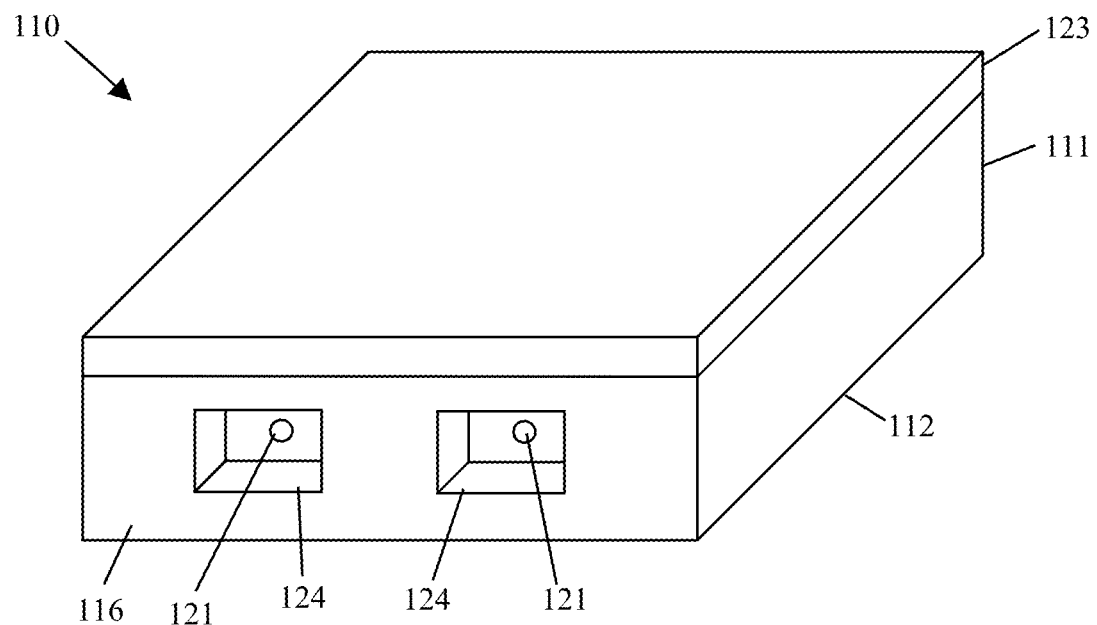
FIG. 28 is a perspective view of a safety-blade dispenser according to another aspect of the present disclosure.

The safety blade-dispenser 14 described above comprises one example of a sharps dispenser that is specifically configured (by way of example) to safely contain and eject surgical sharps 310 in the form of scalpel blades that must be subsequently attached to a handle prior to use in surgery. In some instances, however, it may be beneficial to select and eject a cutting instrument with the blade and handle pre-assembled (or integrally formed). FIGS. 25-26 illustrate one example of a surgical sharps dispenser 454 configured to safely contain and selectively eject one or more larger surgical sharps, such as a complete scalpel 456 including a handle 458 and a blade 460 shown by way of example in FIG. 27.

The surgical sharps dispenser 454 of the present example is similar in form and function to the safety blade-dispenser 14 described above such that identical features will not be described a second time. However it should be understood that any of the features described above in regard to safety blade-dispenser 14, alone or in combination, may be applied to the surgical sharps dispenser 454 without reservation. Generally, the surgical sharps dispenser 454 described herein by way of example comprises a generally rectangular container having a storage portion and a handle portion, the storage portion including four surgical sharps holder assemblies arranged side-by-side in a 1×4 matrix configuration. The holder assemblies are slideable in the same direction such that all four surgical sharps are removed on the same side of the device.

The surgical sharps dispenser 454 of the present example includes a housing 462 comprising at least one sharps holder assembly 464 configured to releaseably hold a surgical sharp (e.g. scalpel 456). Preferably, the surgical sharps dispenser 454 includes a plurality of sharps holder assemblies 464. By way of example only, the surgical sharps dispenser 454 described herein includes four sharps holder assemblies 464, however any number of sharps holder assemblies 464 is possible. The sharps holder assemblies 464 are moveable between a first position in which the surgical sharp 456 is fully contained within the housing 462 (e.g. FIG. 23) and a final position in which at least a portion of the surgical sharp 456 is protruding from the housing 462 (e.g. FIG. 24) to enable removal of the surgical sharp 456 from the housing 462. By way of example, the movement may be unidirectional or bidirectional.

The housing 462 is generally compact in size, allowing the surgical sharps dispenser 454 to be held and operated in the palm of a single user's hand, while being large enough to contain and dispense at least one surgical sharp 456. Like the housing 302 of the surgical sharps dispenser 300 described above, the housing 462 is generally rectangular in shape with rounded and/or scalloped edges 466 for ease of gripping. The housing 462 further includes an extended proximal end 468 to accommodate larger surgical sharps such as the scalpels 456 of the present example. The housing 462 further has an interior cavity in which the sharps holder assemblies 464 and surgical sharps 456 reside. The sharps 456 emerge from the interior cavity through openings formed within the distal end 470 of the housing 462, with the proximal end 472 of the scalpel 454 being presented for removal from the sharps holder assembly 464 for subsequent use in the surgical procedure.

Figure 31:
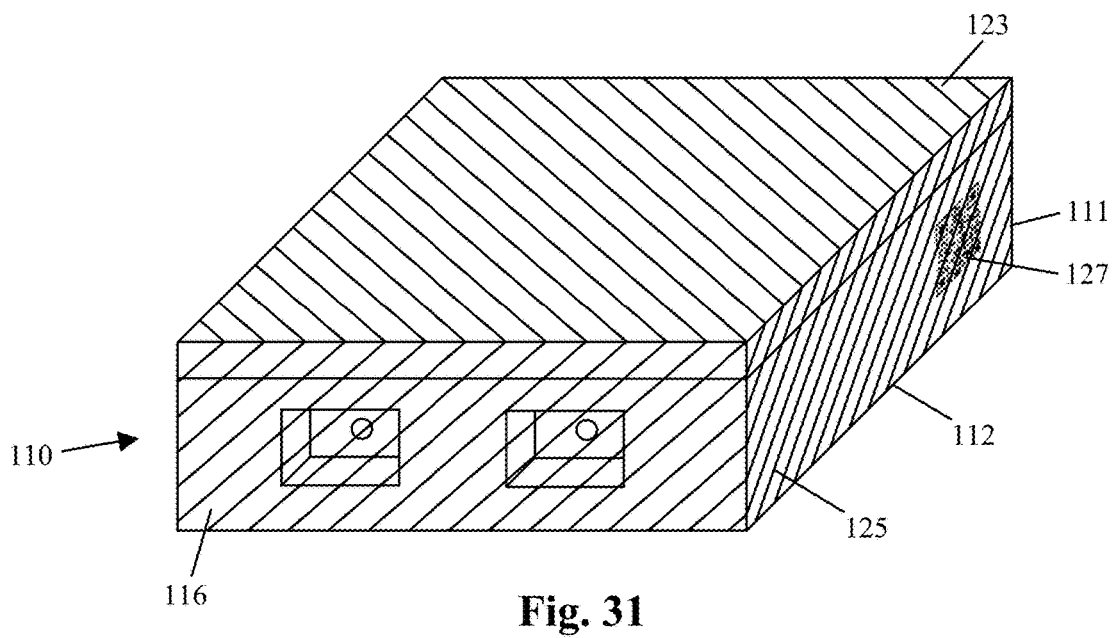
FIG. 31 is a perspective view of the safety-blade dispenser of FIG. 28 with an external covering material and a tracking component.
Figure 32:
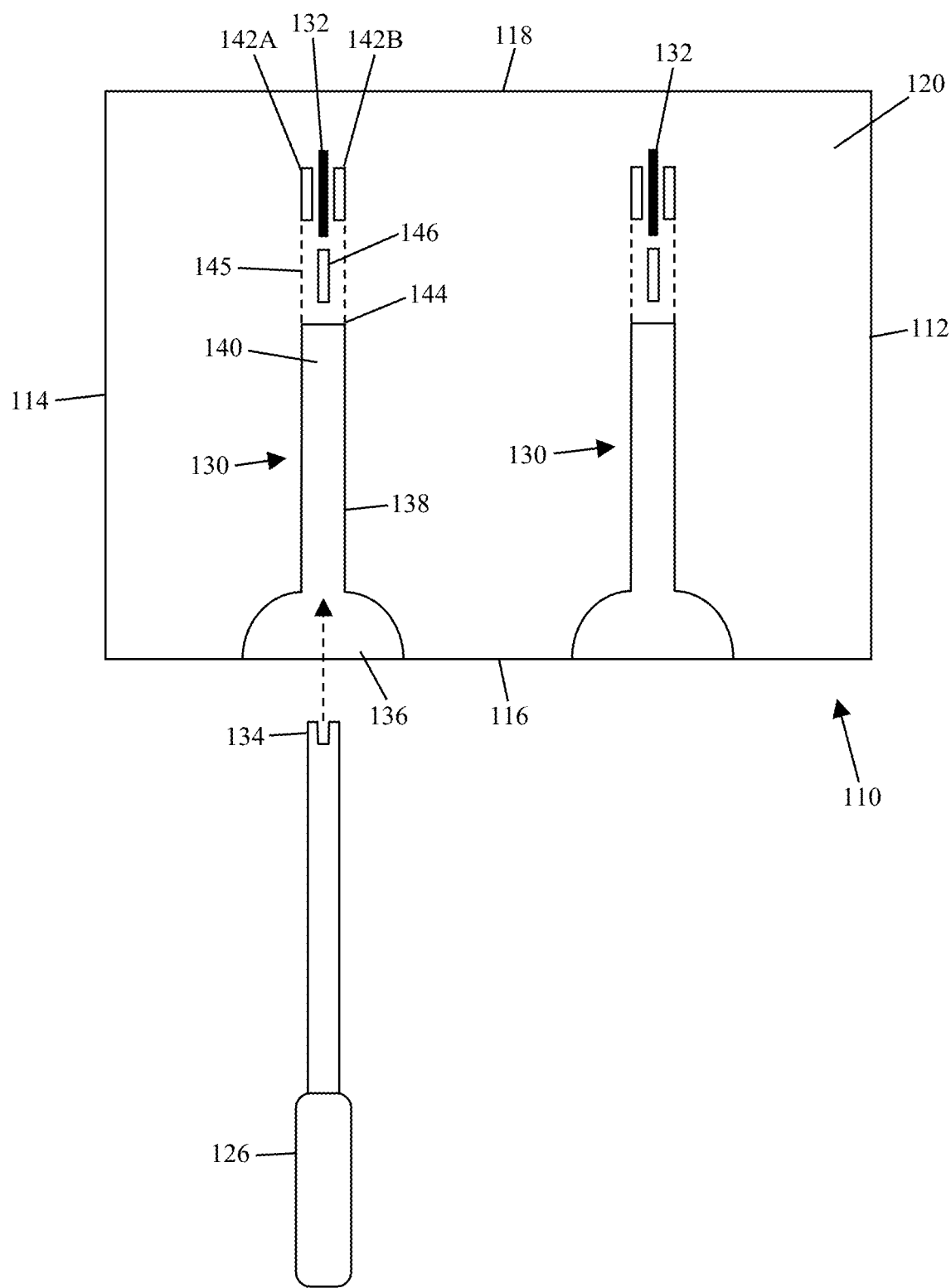
FIG. 32 is a cross-sectional view of the safety-blade dispenser of FIG. 28.

FIGS. 28-33 illustrate an alternate safety-blade dispenser 110 for safely storing surgical blades according to an aspect of the present disclosure. The surgical blade storage container 110 comprises a lower portion 111 comprising a first set of opposing side walls 112 and 114 arranged in a generally parallel orientation, and a second set of opposing end walls 116 and 118. The end walls 116 and 118 are arranged in a generally parallel orientation. A bottom wall 120 connects side walls 112 and 114 and end walls 116 and 118 to form an interior 122, see FIG. 30. The arrangement of the side walls 112, 114, end walls 116, 118, and the bottom wall 120 forms a partially enclosed structure. An upper portion 123 secures to the side walls 112, 114 and end walls 116, 118 to form an enclosed structure. Preferably, the upper portion 123 and the lower portion 111 are sealed together to form a single unit. A material 125, indicated as diagonal lines shown in FIG. 31, may be used to maintain the surgical blade storage container 110 as a sterile component. The material 125 may be a sterile plastic or paper wrap sized and shaped to cover the entire surgical blade storage container 110. Alternatively, the material 125 may be applied to one or more portions of the surgical blade storage container 110. The surgical blade storage container 110 may further include a tracking mechanism or monitoring mechanism. As seen in FIG. 31, positioned on side wall 112 is a tracking and/or monitoring mechanism using, for example, a data capture and/or display device or system or other digital information options, illustrated herein as a Quick Response Code (QR code) 127. Alternatively, a bar code (an optical machine-readable representation of data) such as a Universal Product Code (UPC) may be used. The QR code can be programmed with various patient identifying information similar to that of the labels described previously, including the patient name or other identification means, type of surgery, site of surgery, and physician name. As such, when a physician or medical support team member scans the QR code 127 with a bar code reader, scanner, or camera, they will be able to view the information. The surgical blade storage container 110 may also utilize an alternative embodiment of a tracking and/or monitoring mechanism, such as radio-frequency identification (RFID) transponder.

The RFID transponder generally comprises a chip for storage and/or processing, an antenna for transmitting and receiving information, and an inlay for supporting the chip and antenna. While any RFID transponder known to one of skill in the art may be used, the RFID transponder may be an active tag having a battery which runs the microchip circuitry or a passive tag without a battery and using a RFID reader which is designed to send electromagnetic waves to induce the tag's antenna to power the microchip circuitry. The transponder may be a read-only tag which contains data pre-written thereon, a write-once tag which allows the user to write data to the tag one time, or a full read and write tag which enables the user to write new data to the transponder as needed. The inlay may be a substrate film which can support and hold the chip and antenna. Alternatively, the inlay can be a label or tag having self-adhesion coating to ensure that the RFID chip and antenna adhere to a surface. The inlay may be embedded in plastic castings or casted in polyurethane resin coating.

Referring back to FIG. 28, the surgical blade storage container 110 comprises at least one surgical blade inlet entrance 124, illustrated herein as a recessed or set back region. The at least one surgical blade inlet entrance 124 contains an opening 121 which allows a blade handle 126 (see FIG. 32) to move through end wall 116 and into and out of the interior region 122. The at least one surgical blade inlet entrance 124 is sized and shaped to allow at least a portion of the surgical blade handle 126 to fit within upon insertion. In addition, the at least on surgical blade inlet entrance 124 may also be sized and shaped to accommodate a blade handle having a surgical blade attached thereto upon removal. The opening 124 leads to a guide member, referred to generally as a surgical blade handle guide 130. The surgical blade handle guide 130 is designed to guide at least a portion of the surgical blade handle 126 to a surgical blade 132 stored within. As such, upon insertion of the surgical blade handle 126, the distal end 134, i.e. the end which connects to, and holds a surgical blade, is automatically guided to where the surgical blade is positioned, thereby preventing the user from direct contact with the surgical blade upon connection.

Figure 29:
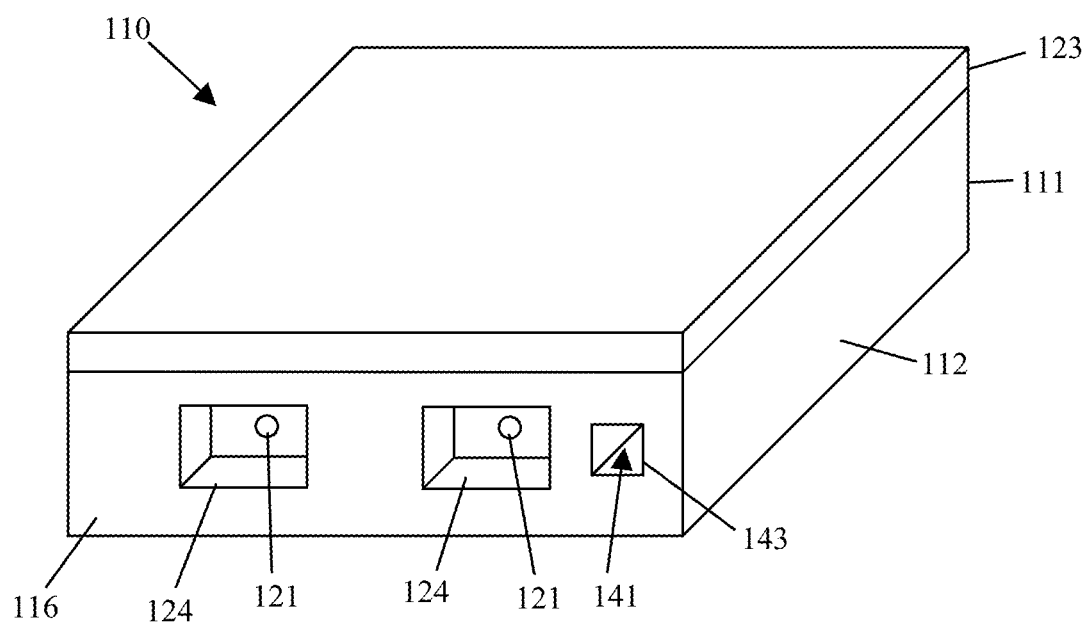
FIG. 29 is a perspective view of the safety-blade dispenser of FIG. 28 with an optional feature of a blade handle recess according to an aspect of the present disclosure.
Figure 30:
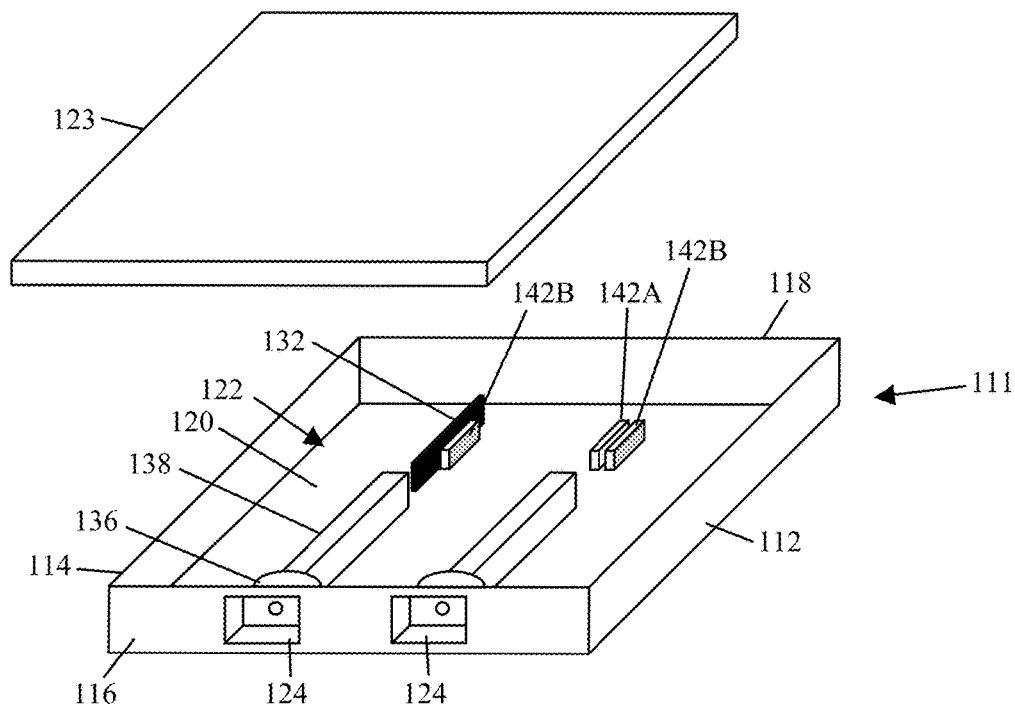
FIG. 30 is an exploded view of the safety-blade dispenser of FIG. 28.
Figure 33:
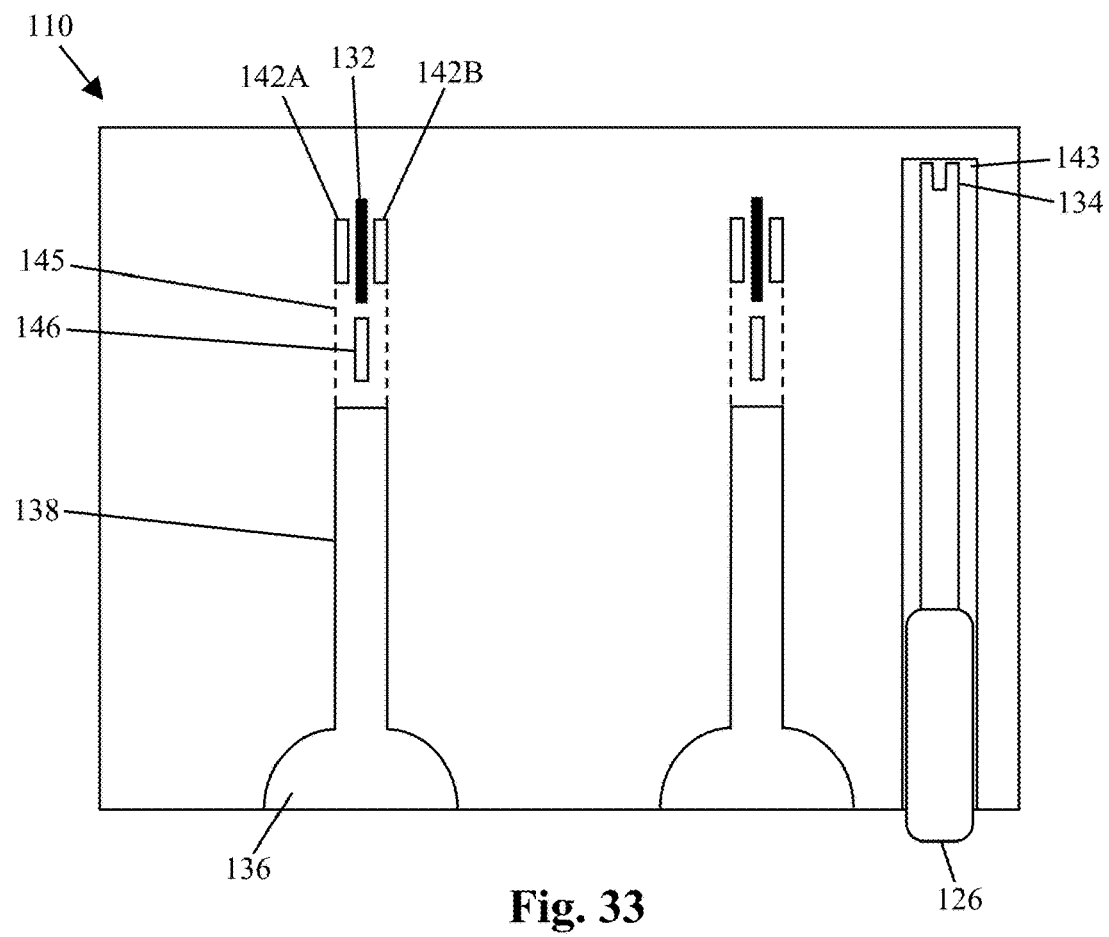
FIG. 33 is a cross-sectional view of the safety-blade dispenser of FIG. 29.

FIG. 29 illustrates the surgical blade storage container 110 having an additional feature of a surgical blade handle storage lumen 141 (see also FIG. 33). The surgical blade handle storage lumen 141 is sized and shaped to receive and store the surgical blade handle 126 (see FIG. 33) through opening 143.

The surgical blade handle guide 130 contains a blade inlet 136. The blade inlet 136 is sized and shaped to guide the surgical blade handle 126 towards a blade channel 138. The blade inlet 136, therefore, may be configured to contain a larger outer area which is directed towards or is angled towards the blade channel 138. Such arrangement allows the user a greater degree of freedom to insert the surgical blade handle into the at least one surgical blade inlet entrance 124 and the blade inlet 36 and ensure alignment with the surgical blade 132. The blade channel 138 is shown as an elongated tubular structure having an interior lumen 140 constructed to receive at least a portion of the surgical blade handle 126 to provide further guidance towards the surgical blade 132.

As the at least a portion of the surgical blade handle 126 moves through the blade inlet 136, the at least a portion of the surgical blade handle 126 is directed to the surgical blade so that the surgical blade handle distal end 134 aligns with a portion of the surgical blade that connects thereto. The surgical blade 132 may contain one or more maintenance structures, illustrated as walls 142A and 142B, which maintain the surgical blade 132 in a proper orientation or location, such as parallel to wall 120, at an angle to wall 120, or in alignment with an open end 144 of the blade channel 138. If required, a blade coupler 146 may be positioned between the distal end of the blade channel 138 and the surgical blade 132. The blade channel 138 may be sized to allow a gap between the distal open end 144 and the surgical blade 132, or may run up to the surgical blade 132 or maintenance structures 142A or 142B, see dashed lines 45.

Figure 34:
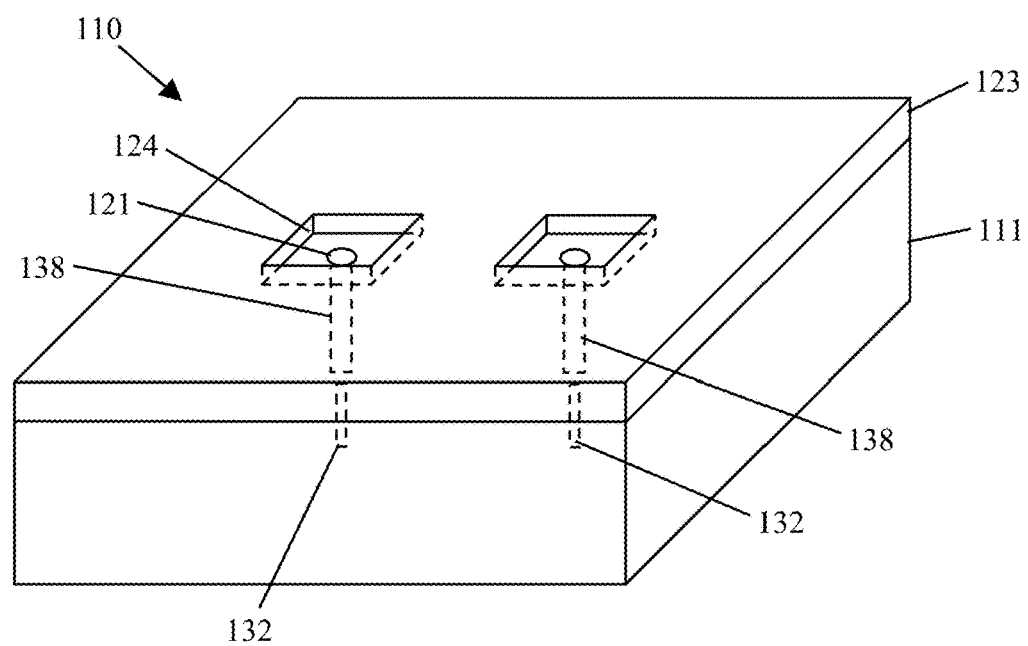
FIG. 34 is a perspective view of a safety-blade dispenser of the type shown in FIG. 28, with alternative placement of the blade inlets.
Figure 35:
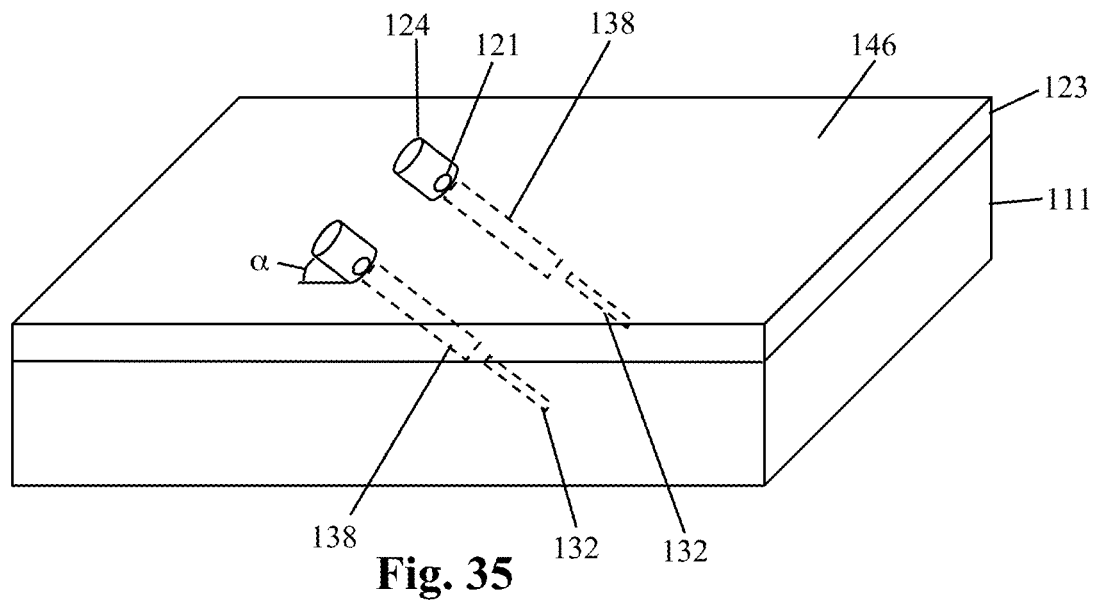
FIG. 35 is a perspective view of a safety-blade dispenser of the type shown in FIG. 28, with alternative placement of the blade inlets.

FIGS. 34-37 illustrate the surgical blade storage container 110 having the at least one surgical blade inlet entrance 124 arranged in different locations or orientations. FIG. 34 shows the at least one surgical blade inlet entrance 124 located on the upper portion 111. In this orientation, the surgical blade handle guide 130 would be arranged in a perpendicular orientation (as opposed to a parallel orientation) relative to wall 120. The surgical blade 132 would be arranged in a perpendicular orientation (as opposed to a parallel orientation) relative to wall 120 as well. FIG. 35 illustrates the at least one surgical blade inlet entrance 124 extending upwardly and outwardly from the outer surface 146 of the upper portion 111. Preferably, the at least one surgical blade inlet entrance 124 is oriented at an angle, a, from the outer surface 146 of the upper portion 111. In this orientation, the surgical blade handle guide 130 would be arranged at an angle (as opposed to a parallel or perpendicular orientation) relative to wall 120. The surgical blade 132 would be arranged at an angle (as opposed to a parallel or perpendicular orientation) relative to wall 120 as well.

Figure 36:
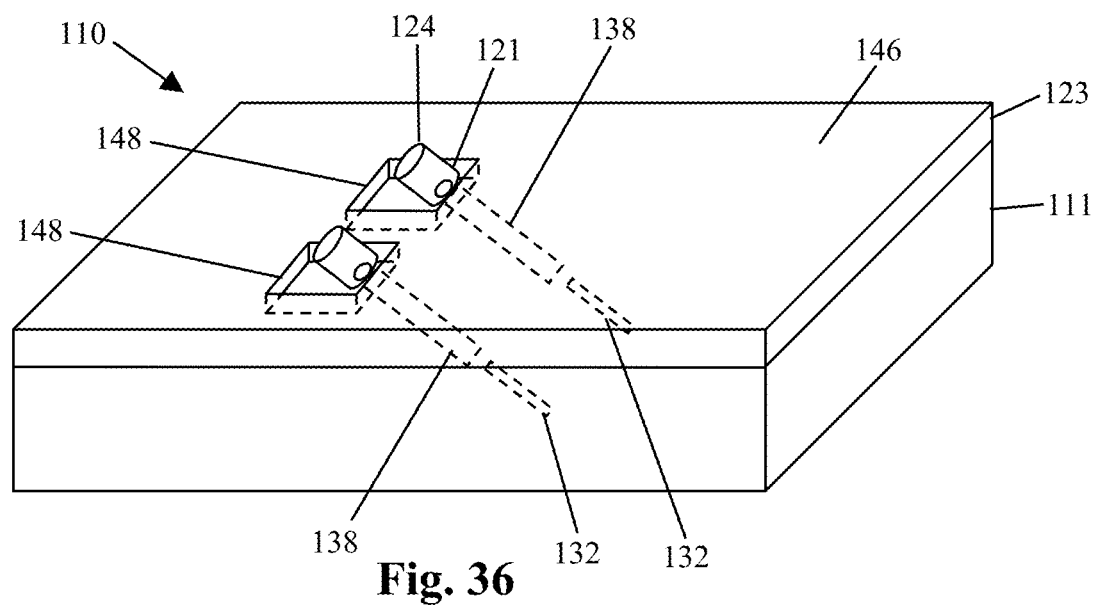
FIG. 36 is a perspective view of a safety-blade dispenser of the type shown in FIG. 28, with rotatable blade inlets shown oriented in a blade-insertion position.
Figure 37:
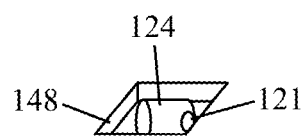
FIG. 37 is a perspective view of rotatable blade inlets shown oriented in a non-insertion position of a safety-blade dispenser of the type shown in FIG. 28.

FIGS. 36-37 illustrate an embodiment of the surgical blade storage container 110 in which the at least one surgical blade inlet entrance 124 rotates or pivots between an open position, FIG. 36, to allow insertion of the surgical blade handle 126, and a closed position, FIG. 37, which prohibits insertion of the surgical blade handle 126. The outer surface 146 of the upper portion 111 may contain a recessed region 148 sized and shaped to accommodate the at least one surgical blade inlet entrance 124 when in the closed position, thereby allowing the at least one surgical blade inlet entrance 124 to be flush with or positioned below the outer surface 146.

Figure 38:
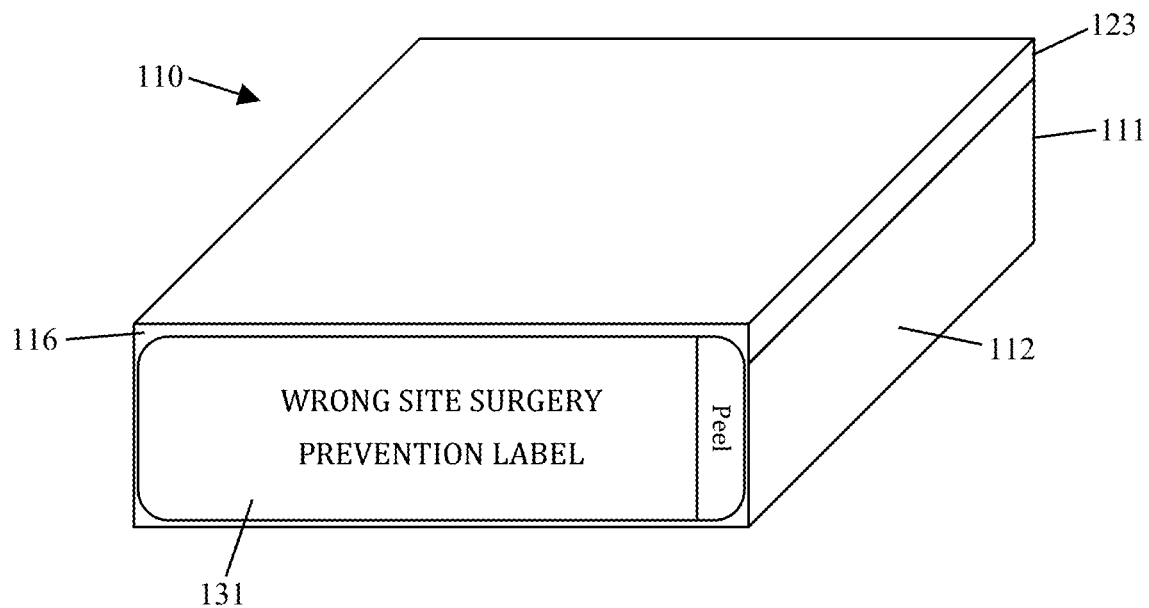
FIG. 38 is a perspective view of a safety-blade dispenser of the type shown in FIG. 28, with a wrong-site surgery prevention label attached to an end wall to cover the blade inlets.

The surgical blade storage container may include a confirmation and signature label 131 (see FIG. 38). The label 131 is removable and covers the at least one surgical blade inlet entrance 124 so access to the surgical blade 132 stored within the surgical blade storage container 110 cannot be obtained until the label is removed. In the embodiment shown in FIG. 38, the confirmation and signature label 131 has a front side that can be written upon and that includes a checklist to be filled out by the surgical technician, in addition to fields where surgical team members sign after confirming that the information entered in the checklist is correct. For example, the checklist preferably provides for confirming the correctness of the patient name, the type/name of the surgical procedure, the laterality of the incision (left, right, or no laterality), and the laterality of the pathology (left, right, midline, or no laterality), and for confirming that the proper instrumentation and any surgical implants are present and accounted for. It will be understood that the confirmation and signature label 131 may be customized for the same or other surgical uses, and thus is not limited to the specific representation depicted herein. Thus, in alternative embodiments, the checklist may call for the same surgery-related information of the depicted embodiment, only some of this information, or additional information.

Preferably, the confirmation and signature label 131 is adhesive-backed and has a pull tab so that it can be easily removed from the surgical blade storage container 110 and, if desired, placed in the medical record (the patient's record/chart/file) after it has been signed and removed. The confirmation and signature label 131 must allow at least the surgeon, or other surgical team members, to fill in the surgical-site information within an input field of the label, i.e. the surgical-site information to conduct a pre-surgery assessment confirming the correct surgical site.

The surgical blade storage container 110 can be configured to provide easy and rapid visualization using a visual indicator to alert the surgical team as to which side (left or right), sometimes referred to as "laterality", of the patient for which a surgical procedure is to take place. All or some portion of the surgical blade storage container 110 may have a color coding of some shade of red, for example as a pink/rose color, to indicate a right side surgical procedure. All or some portion of the surgical blade storage container 110 may have a color coding of some shade of a purple based color, preferably a lavender color, to indicate a left side surgical procedure. Alternative visual indicators may include symbols, letters, words or phrases. In any embodiment, the surgeon or surgical team member can easily ensure that the position of the surgical site or laterality aligns with the color of the container. Gray can be used to indicate neutrality, or no laterality.

Figure 39:
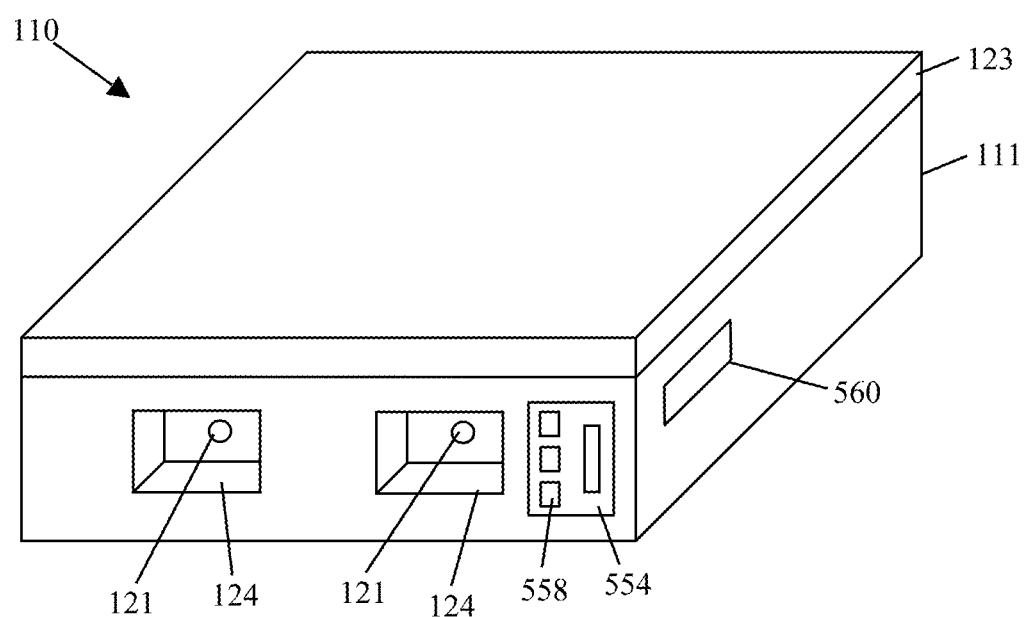
FIG. 39 is a perspective view of a safety-blade dispenser of the type shown in FIG. 28 modified to have a central control unit.
Figure 40:
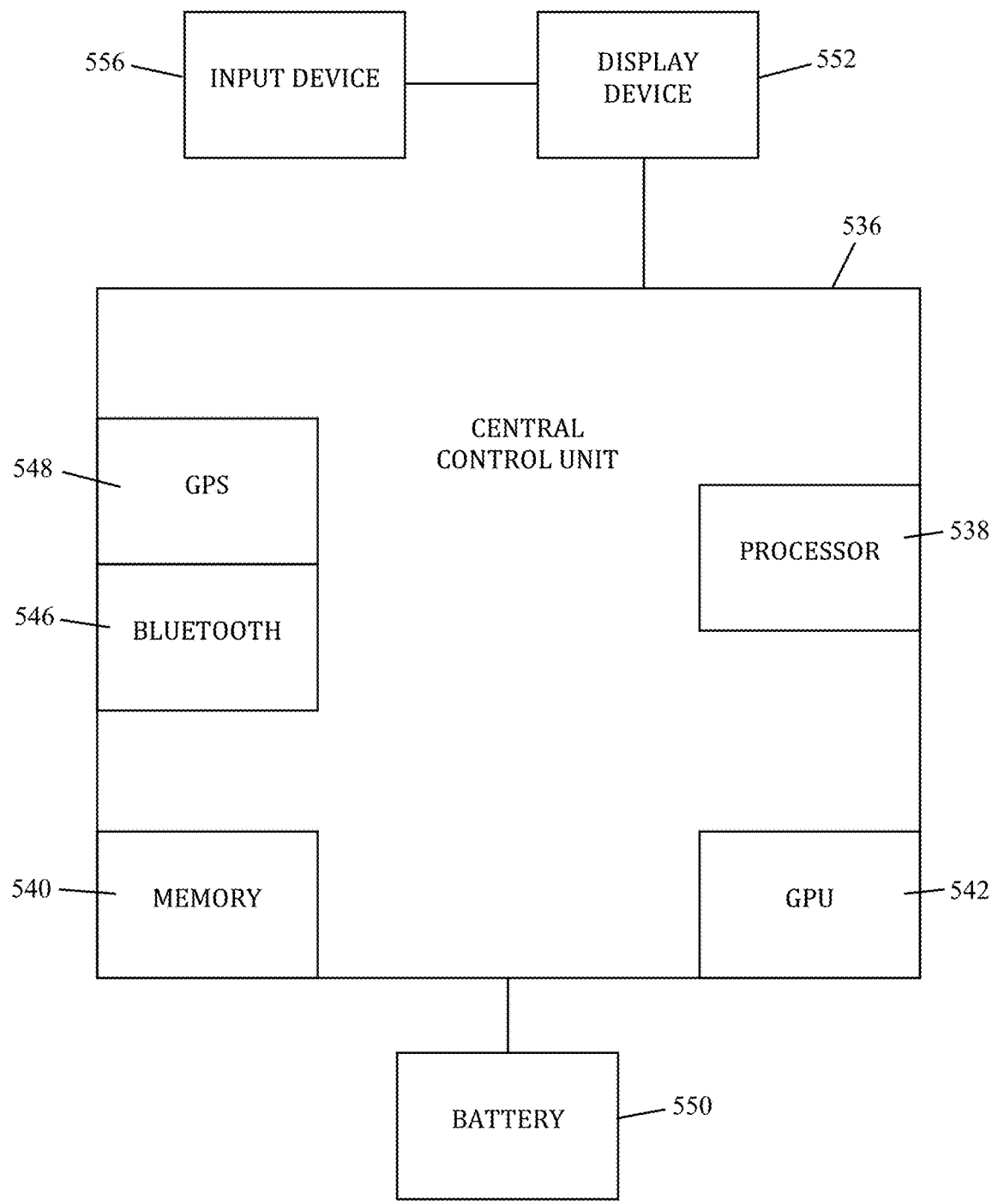
FIG. 40 is a schematic diagram of the components of an illustrative example of a central control unit shown generally in FIG. 39.
Figure 41:
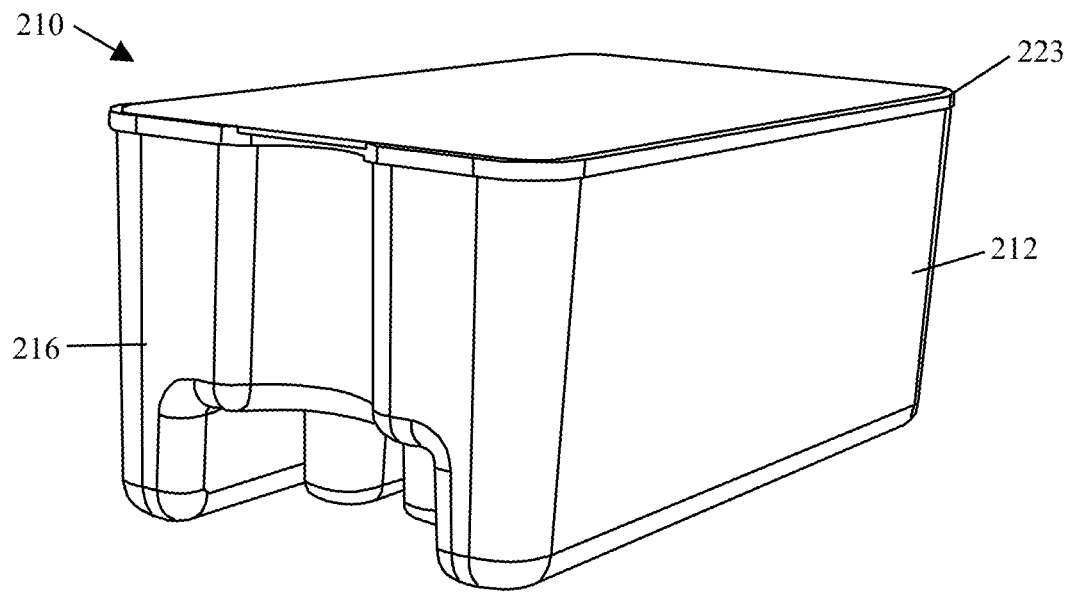
FIG. 41 is a perspective view of an alternate safety-blade dispenser according to the present disclosure.
Figure 42:
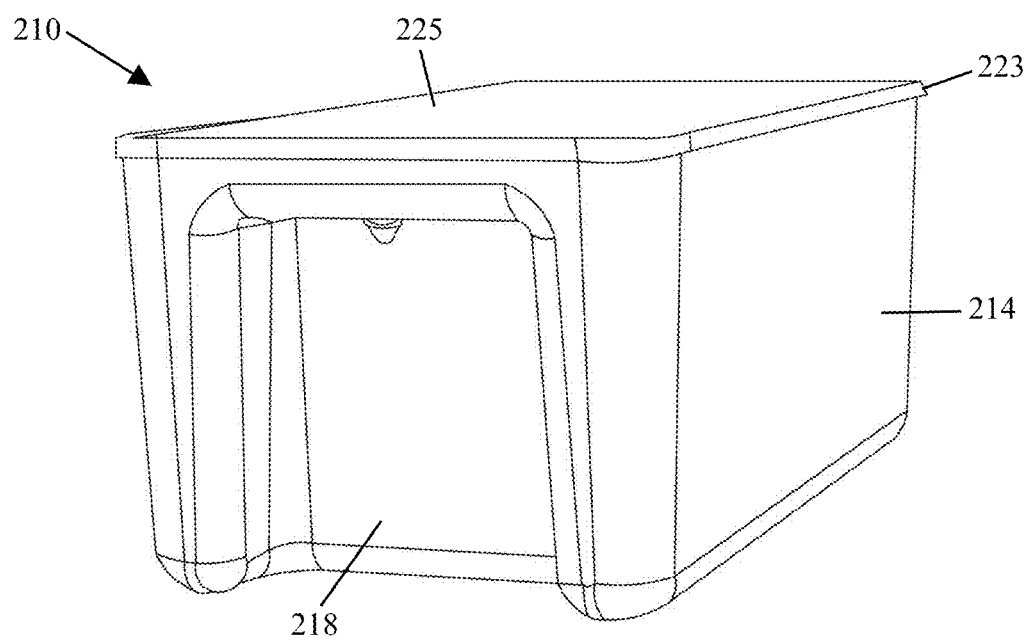
FIG. 42 is an alternative perspective view of the safety-blade dispenser shown in FIG. 41.
Figure 43:
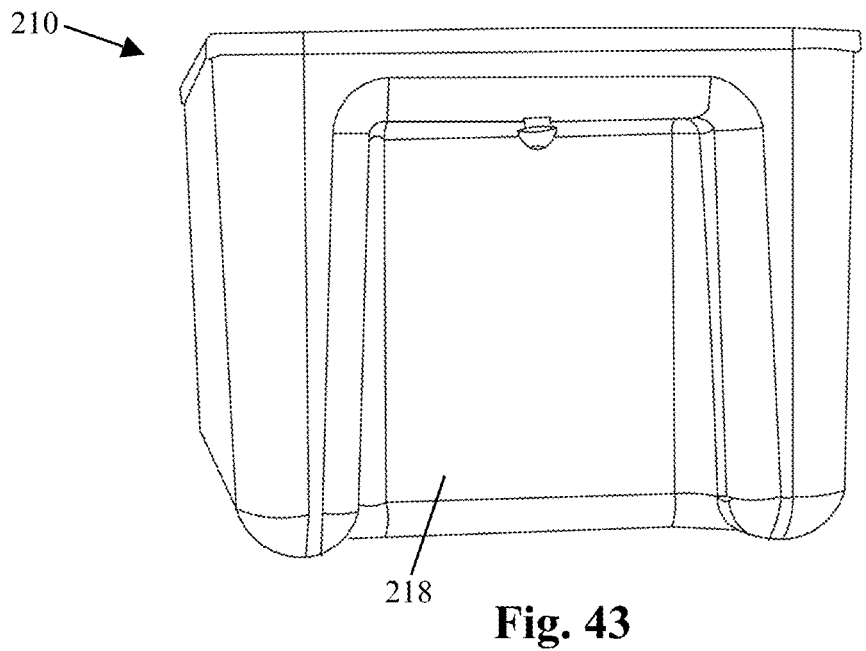
FIG. 43 is a front view of the safety-blade dispenser shown in FIG. 41.
Figure 44:
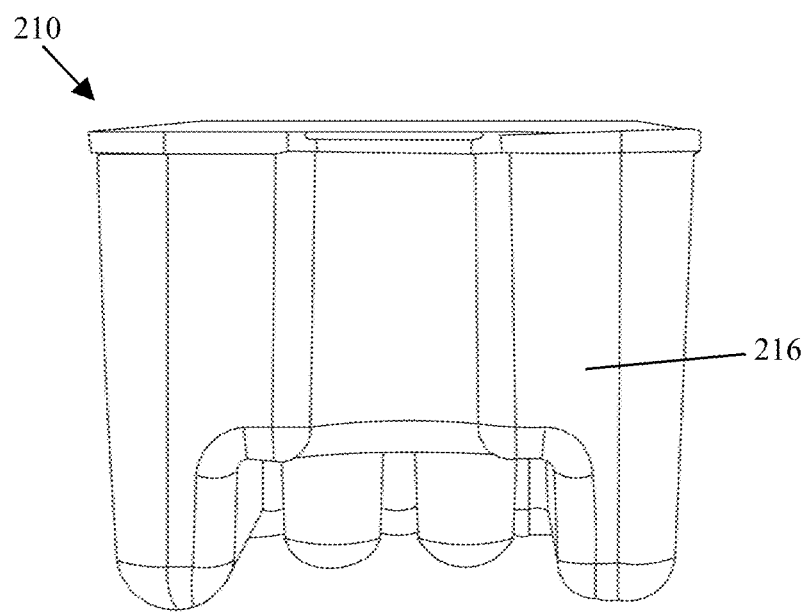
FIG. 44 is a back view of the safety blade container illustrated in FIG. 41.
Figure 45:
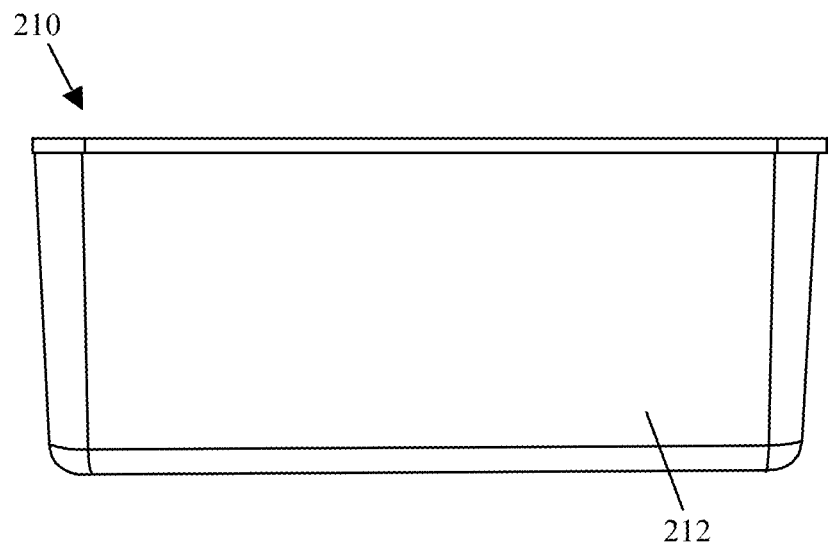
FIG. 45 is a left side view of the safety blade container illustrated in FIG. 41.
Figure 46:
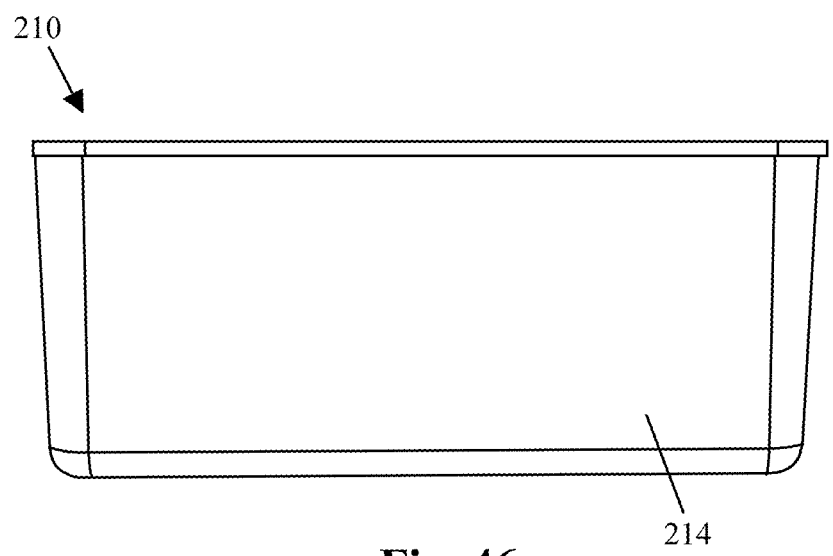
FIG. 46 is a right side view of the safety blade container illustrated in FIG. 41.
Figure 47:
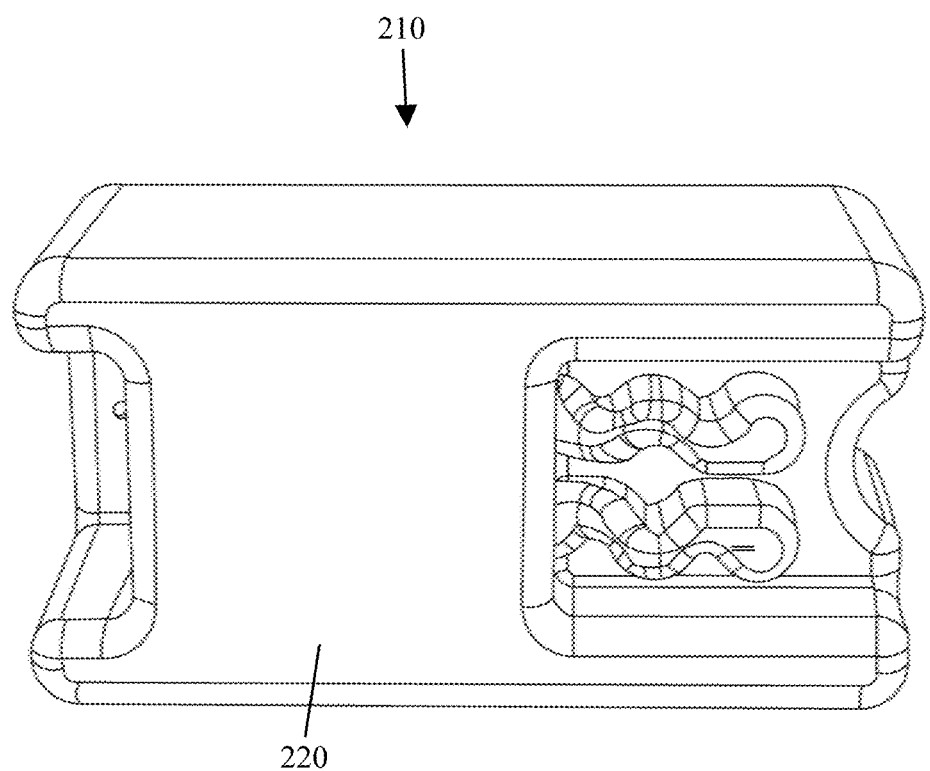
FIG. 47 is a bottom view of the safety blade container illustrated in FIG. 41.
Figure 48:
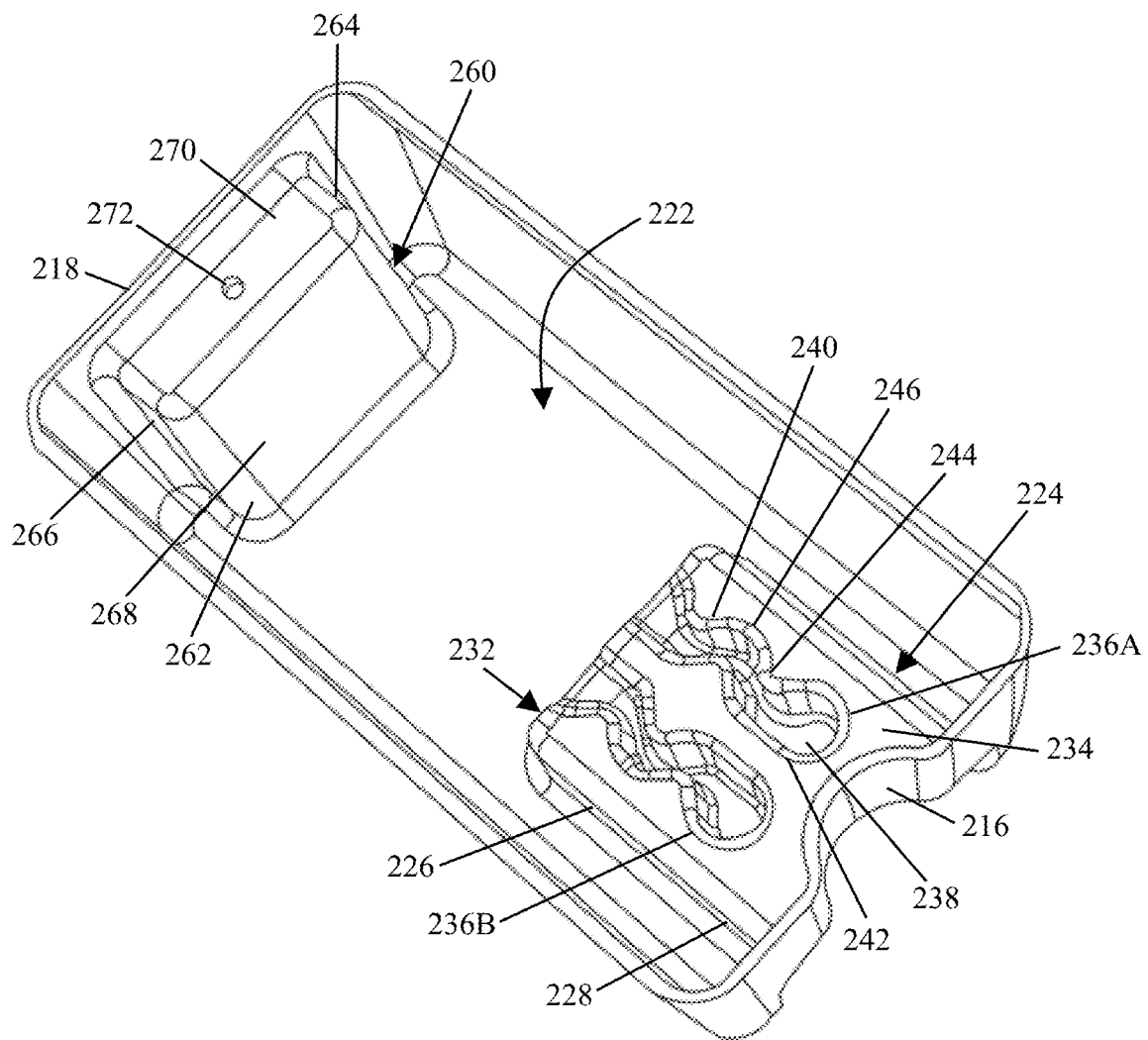
FIG. 48 illustrates the interior of the safety blade container illustrated in FIG. 41.

FIGS. 39 and 40 illustrate the surgical blade storage container 110 converted to a "smart" container. The cover 123 is adapted to include a central control unit 536 including, for example, a processor 538, memory 540, graphic processing unit 542, GPS functioning 548, and Bluetooth wireless capability 546. The central control unit 536 can be powered by a battery 550 and electrically connected to a display unit 552, such as an LED screen 554, see FIG. 39. Data input devices, such as buttons 558 or a keyboard (not shown), may be included to allow the user to input data. The surgical blade storage container 110 may also contain a connection point, illustrated herein as a USB port 560 to allow for transfer of data from the central control unit 536 to a flash drive or a computer system via cables.

The surgical blade storage container 110 can be used in any surgical procedure as a standalone device. In addition, the surgical blade storage container 110 may be a component in a system or method of preventing wrong site surgeries, such as that shown and described in the '210 PCT referenced above.

FIGS. 41-48 illustrate a safety-blade dispenser 210 for safely storing surgical blades according to yet another aspect of the present disclosure. The safety-blade dispenser 210 comprises a lower portion comprising a first set of opposing side walls 212 and 214 arranged in a generally parallel orientation, and a second set of opposing end walls 216 and 218. The end walls 216 and 218 are arranged in a generally parallel orientation. A bottom wall 220 connects side walls 212 and 214 and end walls 216 and 218 to form an interior region 222, see FIG. 48. The arrangement of the side walls 212, 214, end walls 216, 218 and the bottom wall 220 forms a partially enclosed structure. An upper portion, illustrated herein as a cover 223, secures to the side walls 212, 214 to form an enclosed structure. A material 225, such as a removable label, is placed on top of the cover 223. The label may also include a tracking mechanism. As see in FIG. 53, positioned on or with the surgical blade storage container 110 is a tracking and/or monitoring mechanism using, for example, a data capture and/or display device or system or other digital information options, illustrated herein as a Quick Response Code (QR code) 227. Alternatively, a bar code (an optical machine-readable representation of data) such as a Universal Product Code (UPC) maybe used. The QR code can be programmed with various patient identifying information similar to that of the labels described previously, including the patient name or other identification means, type of surgery, site of surgery, and physician name. As such, when a physician or medical support team member scans the QR code 227 with a bar code reader, scanner, or camera, they will be able to view the information. The surgical blade storage container 210 may also utilize an alternative embodiment of a tracking and/or monitoring mechanism, such as a radio-frequency identification (RFID) transponder.

The RFID transponder generally comprises a chip for storage and/or processing, an antenna for transmitting and receiving information, and an inlay for supporting the chip and antenna. While any RFID transponder known to one of skill in the art may be used, the RFID transponder 530 may be an active tag having a battery which runs the microchip circuitry, or a passive tag without a battery and using a RFID reader which is designed to send electromagnetic waves to induce the tag's antenna to power the microchip circuitry. The transponder may be a read-only tag which contains data pre-written thereon, a write-once tag which allows the user to write data to the tag one time, or a full read and write tag which enables the user to write new data to the transponder as needed. The inlay may be a substrate film which can support and hold the chip and antenna. Alternatively, the inlay can be a label or tag having self adhesion coating to ensure that the RFID chip and antenna adhere to a surface. The inlay may be embedded in plastic castings or casted in polyurethane resin coatings.

The surgical system contains the surgical blade storage container 210 which is preferably adapted to be trackable and/or can electronically communicate with other components of the system. The ability to be trackable and/or electronically communicate with other components of the system allows the users of the surgical procedure the ability to continuously monitor and check that the scheduled surgical procedures for a patient is correct, thereby extending the prevention of wrong site surgeries to multiple patient-medical representatives interactions.

The material 223 is removable and covers the lock member (to be described later) so access to unlock the surgical blade storage container 210 until the label is removed is prevented. In one embodiment, for example, the confirmation and signature label 131 has a front side that can be written upon and that includes a checklist to be filled out by the surgical technician, and fields where surgical team members sign after confirming that the information entered in the checklist is correct. For example, the checklist preferably provides for confirming the correctness of the patient name, the type/name of the surgical procedure, the laterality of the incision (left, right, or no laterality), and the laterality of the pathology (left, right, midline, or no laterality), and for confirming that the proper instrumentation and any surgical implants are present and accounted for. It will be understood that the confirmation and signature label 216 may be customized for the same or other surgical uses, and thus is not limited to the specific representation depicted herein. Thus, in alternative embodiments, the checklist may call for the same surgery-related information of the depicted embodiment, only some of this information, or additional information. Preferably, the confirmation and signature label 231 is adhesive-backed and has a pull tab so that it can be easily removed from the container 212 and, if desired, placed in the medical record (the patient's record/chart/file) after it has been signed and removed. The confirmation and signature label 231 must allow at least the surgeon, or other surgical team members, to fill in the surgical-site information within an input field of the label, i.e. the surgical-site information to conduct a pre-surgery assessment confirming the correct surgical site.

The interior 222 of the surgical blade storage container 210 is configured to provide a mechanism to secure a surgical instrument, such as a surgical blade, therein in a predetermined orientation. Positioned towards the end wall 216 is a surgical instrument holding member 224. While the surgical instrument holding member 224 is shown configured to hold two surgical instruments, such number is illustrative only as the surgical instrument holding member 224 can be configured to hold one surgical instrument or more than two surgical instruments.

The surgical instrument holding member 224 comprises a main body 226 formed by a plurality of side walls 228, 230, 232 and an upper wall 234. Two surgical instrument receiving areas 236A and 236B are configured to receive and hold a surgical instrument. Surgical instrument receiving area 236A comprises an open slotted channel 238 defined by a first wall 240 and a second opposing wall 242. Each of the walls 240 and 242 are irregularly shaped to contain a plurality of concave portions 244 directed inwardly, or towards the slotted channel 238, and convex portions 246 directed outwardly, or away from the slotted channel 238. As shown in the figure, each wall 242 or 244 has a plurality of concave portions 244 and convex portions 246. In some areas of the surgical instrument receiving area 236A, where a concave portion 244 is formed in one wall, a corresponding convex portion is 246 is formed in the opposite wall. In this manner, one or more concave portions 244 align with one or more convex portions 246. The concave portions 244 in each of the walls 240 and 242 provide contact points for maintaining the positioning or orientation of surgical equipment placed within the surgical instrument receiving area 236A.

Figure 49:
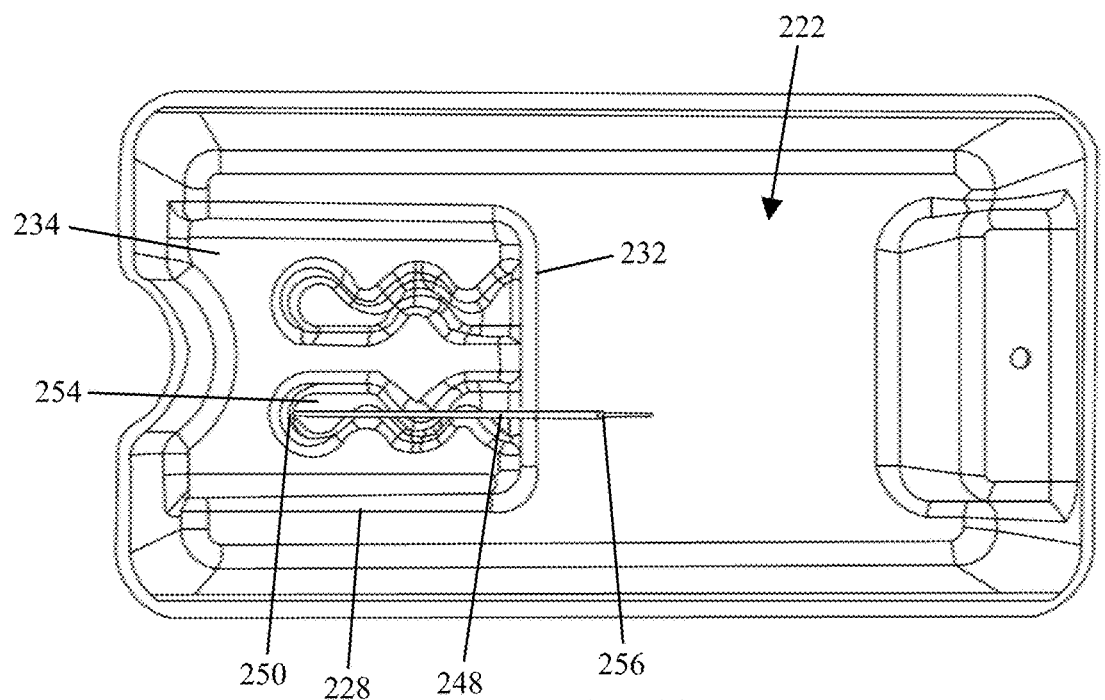
FIG. 49 illustrates the interior of the safety blade container illustrated in FIG. 41 and having a surgical blade secured therein.
Figure 50:
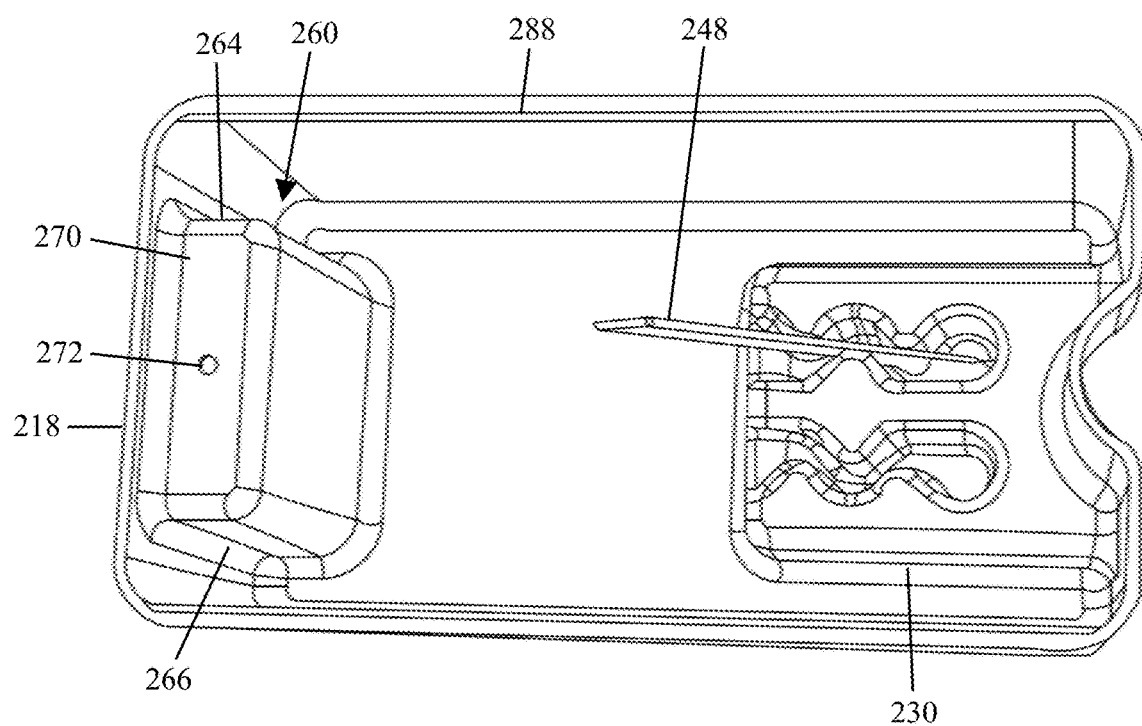
FIG. 50 is an alternative view of the interior of the safety blade container illustrated in FIG. 41 and having a surgical blade secured therein.
Figure 51:
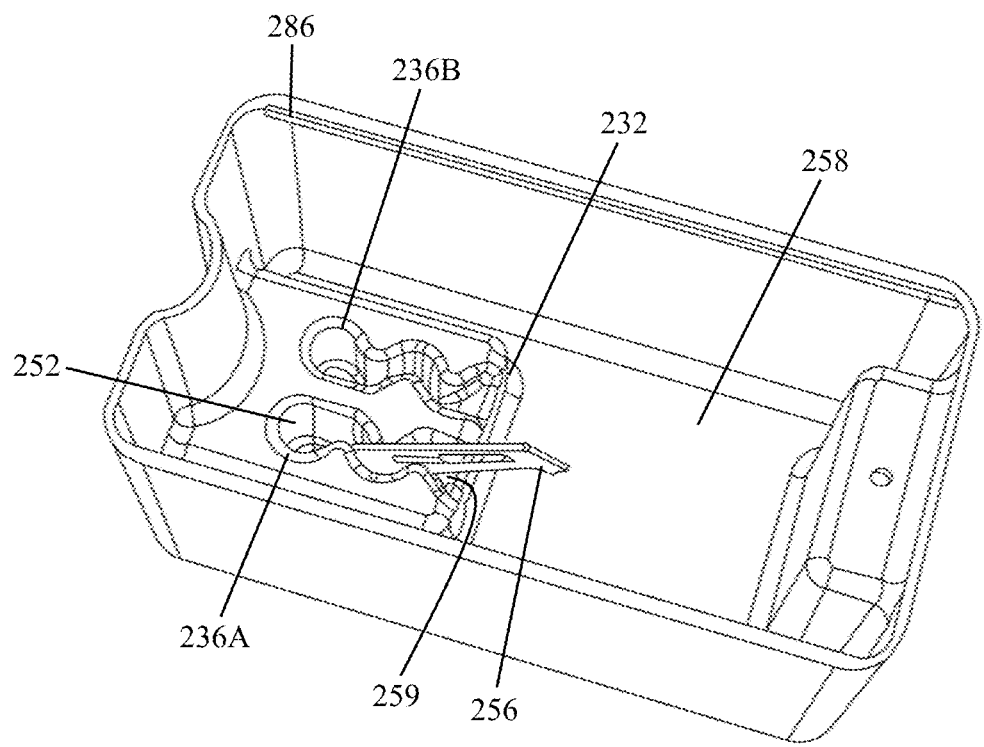
FIG. 51 is an alternative view of the interior of the safety blade container illustrated in FIG. 41 and having a surgical blade secured therein.

Referring to FIGS. 49-51, the surgical instrument receiving area 236A is shown storing/holding a surgical blade 248. A sharp or pointed edge 250 of the surgical blade 248 rests against a back wall 252 (see FIG. 51) with the cutting edge (not shown) resting against bottom surface 254. The connecting end 256 (i.e. the end that connects to a surgical cutting tool handle) of the surgical blade 248 simultaneously rests against an opposing front wall 259. The front wall 259 preferably is angled to allow the surgical blade 248 to be positioned in a particular orientation to allow a user to easily attach a surgical tool handle to the surgical blade 48 without the user having to handle the surgical blade 248 with his/her hands. This orientation, therefore, positions the surgical blade 248 so that the one end, the connecting end 256, extends up from, or is positioned above the surgical blade storage container 210 inner surface 258 or the bottom surface 254 of the surgical instrument receiving area 236A, and the other blade end, i.e., the sharp or pointed edge 250, rests at the bottom surface 254 of the surgical instrument receiving area 236A. Preferably, the surgical blade 248 is orientated at an angle from the surgical blade storage container 210 inner surface 258 and the bottom surface 254 of the surgical instrument receiving area 236A. The surgical blade storage container 210 inner surface 258 and the bottom surface 254 of the surgical instrument receiving area 236A could be the same. The surgical instrument receiving area 236B has an identical configuration as that of the surgical instrument receiving area 236A.

Positioned near wall 218 is a lid locking member 260. The lid locking member 260 comprises a main body 262 having two opposing side walls 264 and 266 separated by a front wall 268. A top wall 270 contains a locking receiving component, illustrated herein as an opening 272. The opening 272 is sized and shaped to receive at least a portion of a locking member (to be described later) associated with cover 223.

Figure 52:
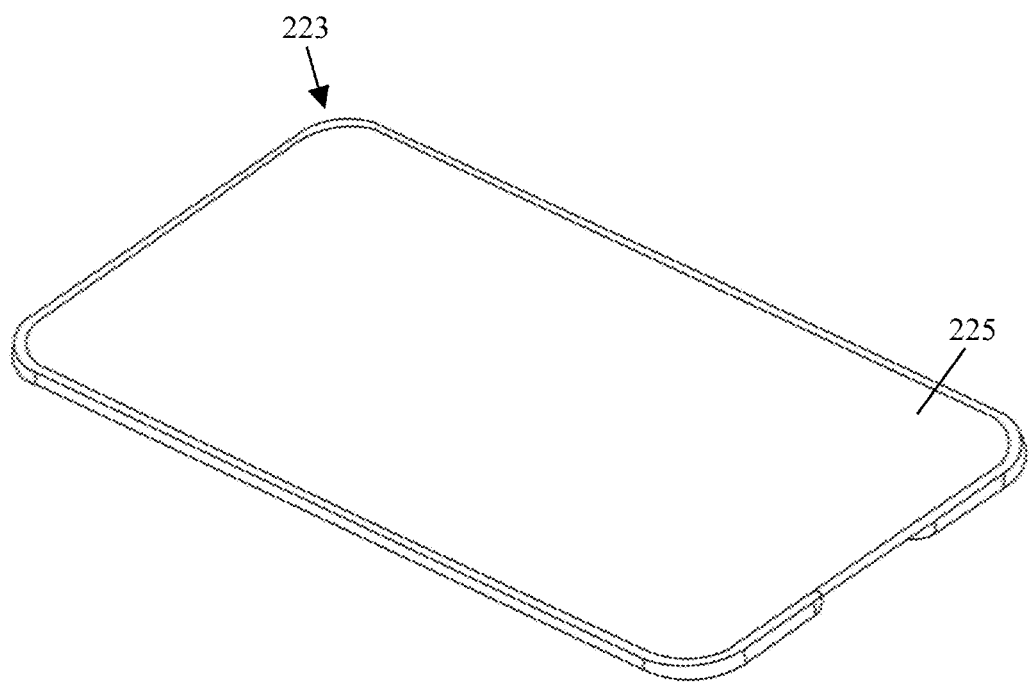
FIG. 52 is a top perspective view of an illustrative example of a safety blade container cover.
Figure 53:
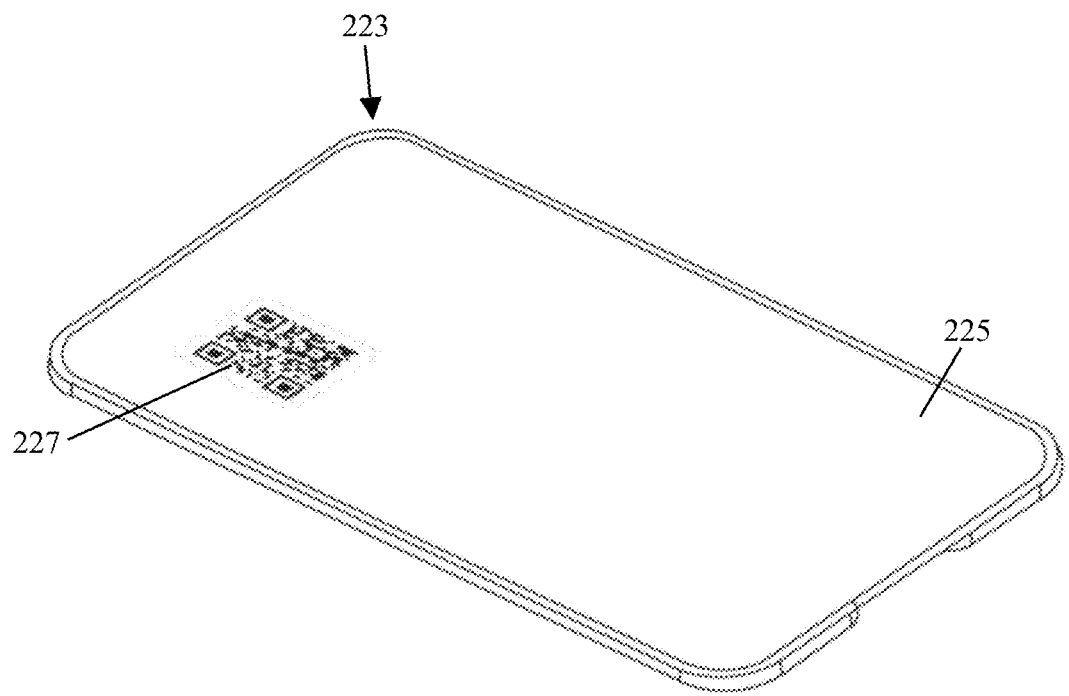
FIG. 53 is a top perspective view of an illustrative example of a safety blade container cover having a QR code.
Figure 54:
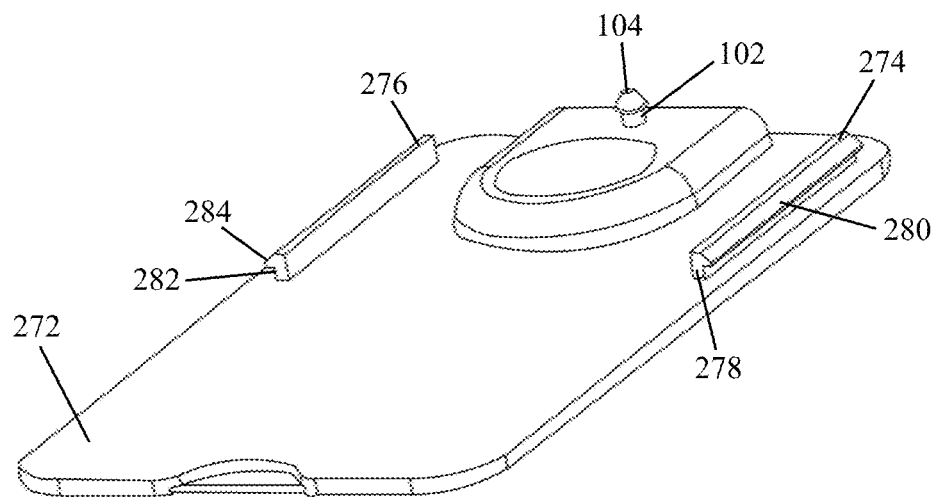
FIG. 54 is a perspective view of the interior surface of the safety blade container cover illustrated in FIG. 52.
Figure 55:
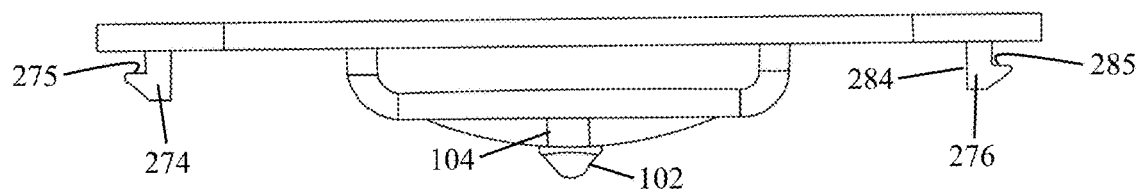
FIG. 55 is a front plan view of the safety blade container cover.
Figure 56:
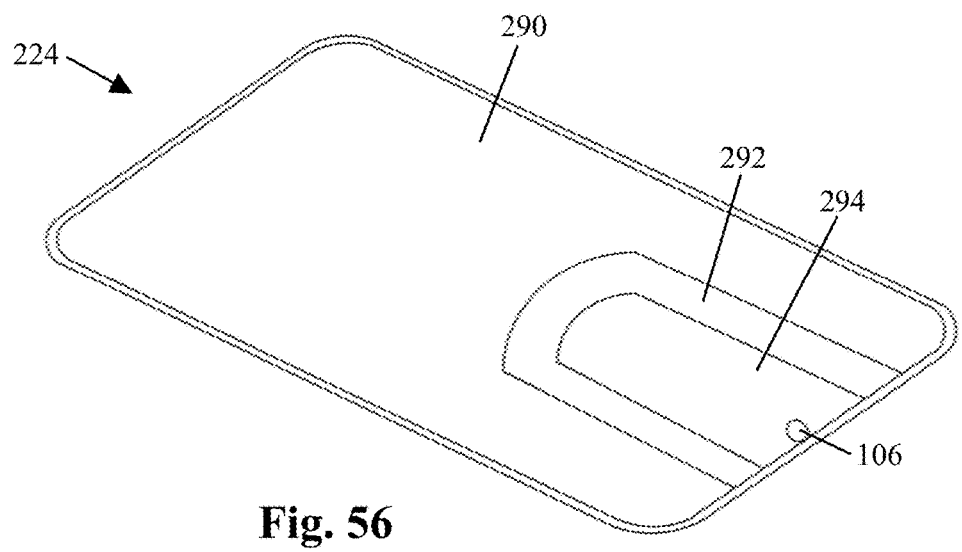
FIG. 56 is a top perspective view of the safety blade container cover illustrating the locking receptacle without a locking pin.
Figure 57:
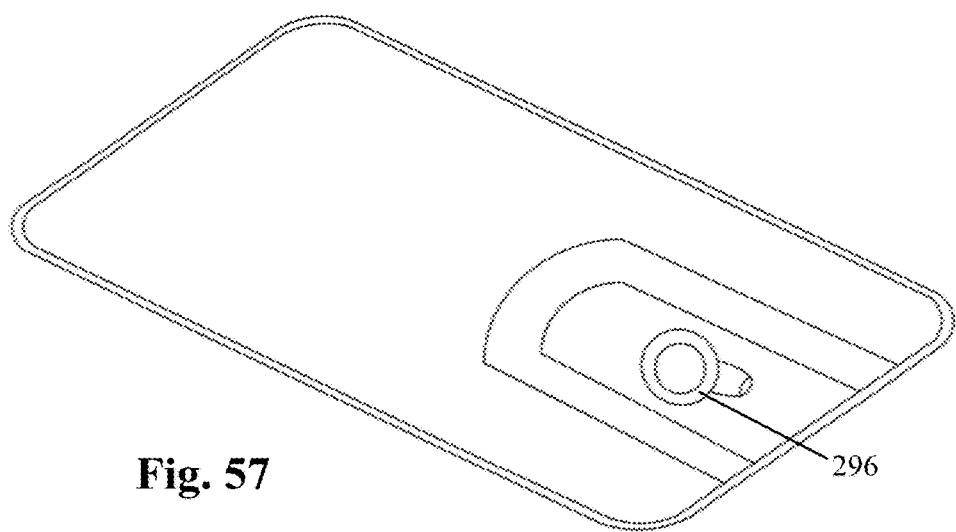
FIG. 57 is a top perspective view of the safety blade container cover illustrating the locking receptacle with a locking pin.

Referring to FIGS. 52-54, an illustrative example of the cover 223 is shown. The cover 223 is configured to slidably engage with the lower portion through engagement with the side walls 212 and 214. An inner surface 272 (see FIG. 53) contains a right guide rail 274 and a left guide rail 276. The right guide rail 274 contains a first portion 278 which extends away from the inner surface 272 and a second portion 280 that extends away from and at an angle from said first portion 278. The second portion 280 contains a first guiding surface 275. The left guide rail 276 contains a first portion 282 which extends away from the inner surface 272 and a second portion 284 that extends away from and at an angle from said first portion 282. The second portion 284 contains a second guiding surface 285. In use, the right guide rail 274 and the left guide rail 276 are positioned so that the first guiding surface 275 and the second guiding surface 285 slidably engage a first lower portion guide member 286 positioned along the length of side wall 212 and a second lower portion guide member 288 positioned along the length of side wall 214, see FIGS. 50 and 51. The second portion 280 of the right guide rail 274 and the second portion 284 of the left guide rail 276, therefore, slide against the first lower portion guide member 286 and the second lower portion guide member 288 as a user slides the cover in a first (forward) or second (reverse) linear direction.

Figure 58:
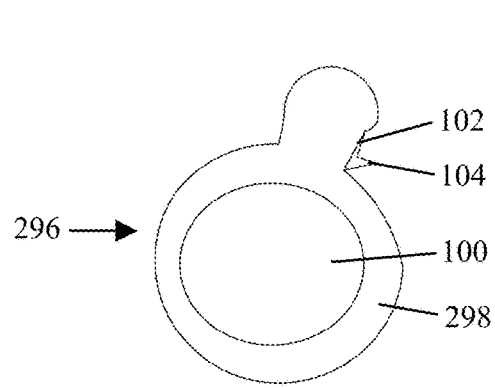
FIG. 58 is a top view of an illustrative embodiment of a locking pin.
Figure 59:
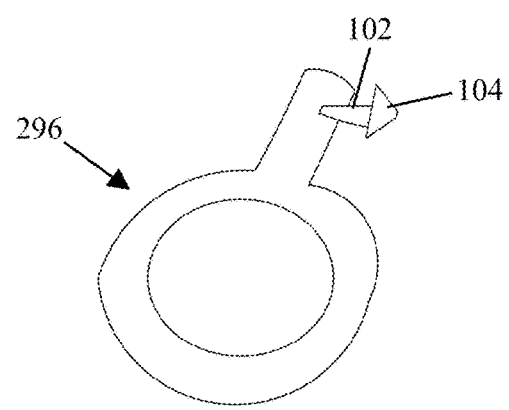
FIG. 59 is a bottom view of the locking pin shown in FIG. 58.

Integrally formed to the front surface 920 of the cover 223 is a locking receptacle 292. The locking receptacle 292 is shown as a U-shaped area having a recessed floor 294 sized and shaped to hold a locking pin 296. FIGS. 58 and FIG. 59 show an illustrative embodiment of the locking pin 296. The locking pin 296 comprises a circular body 298 with an open center section 100. Extending off the circular body 298 is a locking peg 102 having a frustoconical shaped end 104. The locking peg 102 is sized and shaped to fit into opening 106 within the cover 223 and within the locking receiving component opening 272 of top wall 270. As such, when the cover 223 is placed onto the lower portion, opening 106 and opening 272 align together to allow the locking peg 102 to fit within both openings, thereby locking the cover to the side walls 212 and 214.

The surgical blade storage container 210 can be configured to provide easy and rapid visualization using a visual indicator to alert the surgical team as to which side (left or right), sometimes referred to as "laterality", of the patient a surgical procedure is to take place. All of, or some portion of the surgical blade storage container 210 may have a color coding of some shade of red, illustrated herein as pink/rose color hash markings, to indicate a right side surgical procedure. All of, or some portion of the surgical blade storage container 210 may have a color coding of some shade a purple based color, preferably a lavender color, to indicate a right side surgical procedure. Alternative visual indicators may include symbols, letters, words or phases. In any embodiment, the surgeon or surgical team member can easily ensure that the position of the surgical site or laterality aligns with the color of the container. Gray can be used to indicate neutrality, or no laterality.

Figure 60:
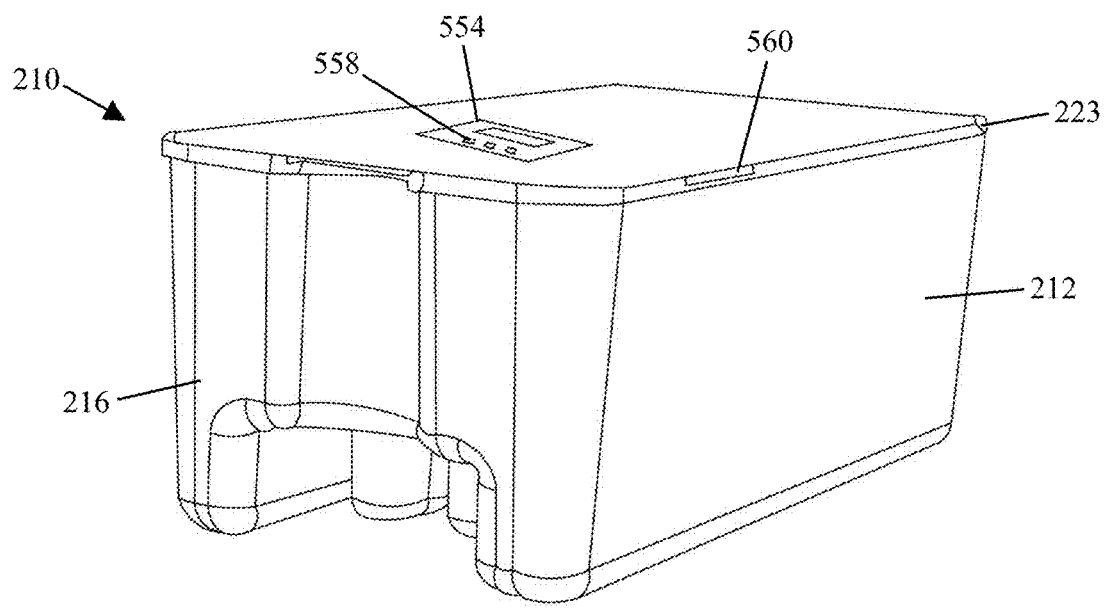
FIG. 60 is a perspective view of a container for surgical equipment according to an alternative embodiment of the invention showing the container having a central control unit.
Figure 61:
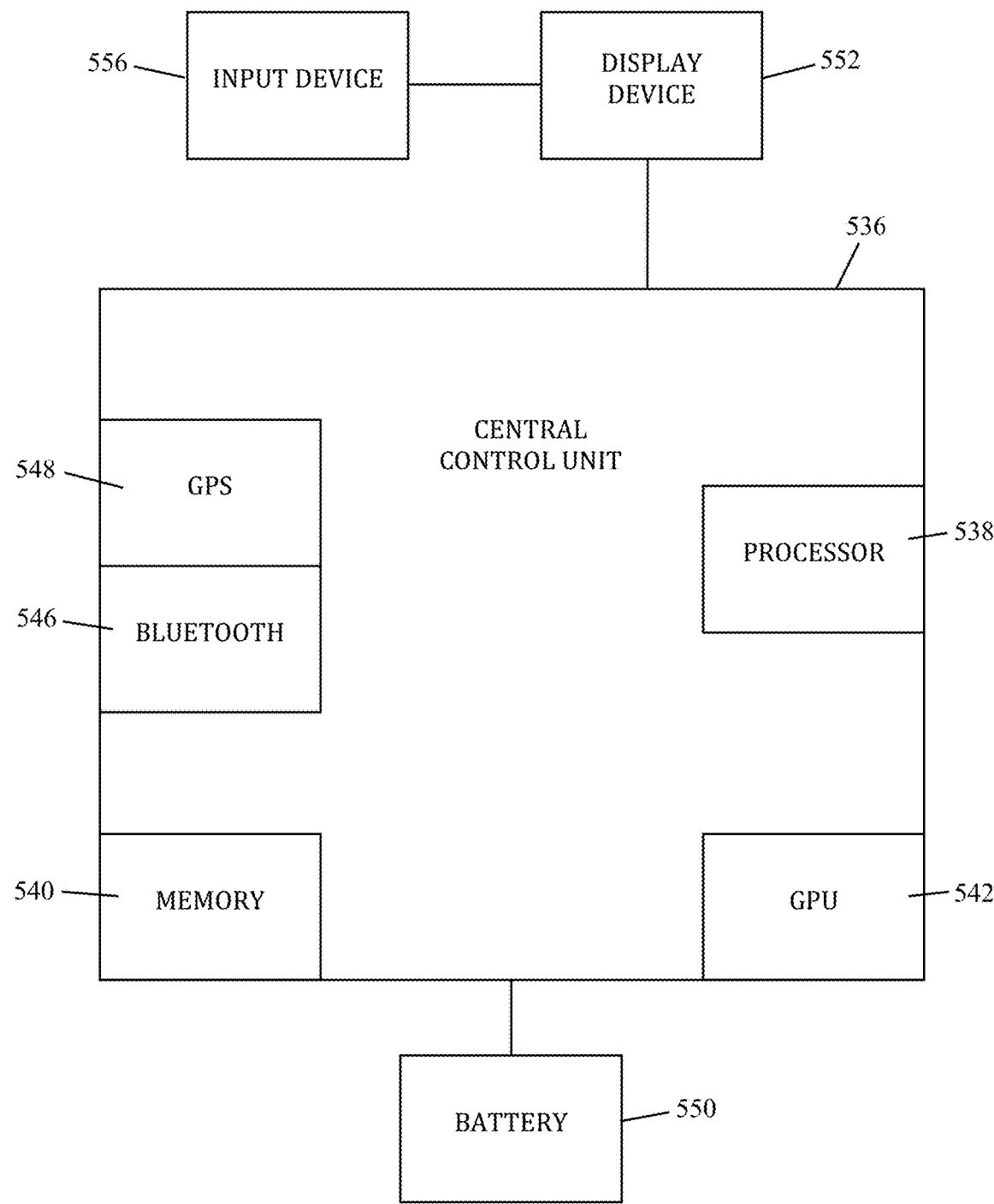
FIG. 61 is a schematic diagram of the components of an illustrative example of a central control unit shown generally in FIG. 60.

FIGS. 60 and 61 illustrate the surgical blade storage container 210 converted to a "smart" container. The cover 223 is adapted to include a central control unit 536 including, for example, a processor 538, memory 540, graphic processing unit 542, GPS functioning 544, and Bluetooth wireless capability 546. The central control unit 536 can be powered by a battery 550 and electrically connected to a display unit 552, such as an LED screen 554, see FIG. 20A. Data input devices, such as buttons 558 or a keyboard (not shown), may be included to allow the user to input data. The surgical blade storage container 210 may also contain a connection point, illustrated herein as a USB port 560 to allow for transfer of data from the central control unit 536 to a flash drive or a computer system via cables.

The surgical blade storage container 210 can be used in any surgical procedure as a standalone device. In addition, the surgical blade storage container 210 may be a component in a system or method of preventing wrong site surgeries, such as the '210 PCT described and incorporated by reference above.

The variously safety-blade dispensers disclosed herein may be provided with a unique container identification number, similar to a vehicle identification number (VIN) used for automobiles. The container identification number (CIN) may be established at the time of manufacture and remains with a particular container. This number is unique to the container in that the number is never reused and never applied to different containers. The unique identification numbers can be integrally formed into the container or may be attached to the container as part of a separate label, or part of the bar code or QR/Scan codes. Once the unique number is assigned to a container and/or is then further correlated or associated to a particular patient, the container as well as the patient information coupled to it is serialized. This allows for the container to be tracked and analyzed as it moves through the medical system. In cases in which a patient has been determined to have wrong information, i.e. the patient should have a right-side surgery, but the box is coded for a left side surgery, the container is destroyed and the reason(s) for its destruction is electronically attached to the unique number. This allows for hospitals or manufactures to review all containers manufactured or scheduled for a medical procedure to determine how many were actually used in such surgical procedures. For those containers not used, reasons as to why containers failed to be used in a medical procedure, potential errors (incorrect/inaccurate manual inputs, near misses), or wrong site surgeries/never events can be reviewed, providing insight as to when, where, and why surgical mistakes were made. Periodical reviews of such data allows hospitals to identify areas that need improvement. The system produces the first accurate and reliable near miss and WSS error data for future data mining, analysis by single and multiple attributes, root cause analysis, to assist hospital system quality control and improvement efforts.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A safety-blade dispenser for use in a surgical procedure, comprising:
   a housing unit sized and configured for holding in a single user's hand, the housing unit having a perimeter defined by first and second opposing panels, first and second opposing ends, and first and second opposing sides, the housing unit further including an interior cavity within the perimeter, the first end including at least one aperture formed therein for dispensing a surgical sharp for use in surgery, and the second end including at least one aperture formed therein for receiving a used surgical sharp after use in surgery; and
   a plurality of surgical blade holder assemblies, each surgical blade holder assembly adapted to releasably hold a respective surgical sharp, at least one surgical blade holder assembly slideably positioned within said interior cavity and moveable between a first position in which the surgical sharp is fully contained within said interior cavity to a second position in which a portion of said surgical sharp protrudes through said at least one aperture formed in the first end,
   wherein the at least one surgical blade holder assembly includes an engagement element configured to engage the surgical sharp while the at least one surgical blade holder assembly is in the first position, the engagement element further configured to disengage the surgical sharp during movement of the at least one surgical blade holder assembly between the first position and the second position.

2. The safety-blade dispenser of claim 1, wherein one of the first and second opposing panels of the housing unit includes a ramped ledge configured to interact with the at least one surgical blade holder assembly.

3. The safety-blade dispenser of claim 1, wherein the plurality of surgical blade holder assemblies are positioned side by side.

4. The safety-blade dispenser of claim 1, wherein said first and second sides include scalloped edges.

5. The safety-blade dispenser of claim 1, wherein said surgical sharp is a surgical blade having a leading end comprising a blade portion and a trailing end comprising a connector portion.

6. The safety-blade dispenser of claim 5, wherein said surgical blade is positioned within said at least one surgical blade holder assembly such that said trailing end protrudes from said housing unit when said at least one surgical blade holder assembly is in said second position.

7. The safety-blade dispenser of claim 1, wherein said surgical sharp is a surgical blade that includes a handle.

8. The safety-blade dispenser of claim 7, wherein said surgical blade and said handle are positioned within said housing unit such that a portion of said handle protrudes from said housing unit when said at least one surgical blade holder assembly is in said second position.

9. The safety-blade dispenser of claim 1, further comprising a confirmation label removably attached to the housing unit, the confirmation label positioned such that movement of the at least one surgical blade holder assembly is prevented while the confirmation label is attached to the housing unit.

10. The safety-blade dispenser of claim 9, wherein a portion of the confirmation label covers at least a portion of the first panel, a portion of the second panel, and a portion of the first end of the housing.

11. The safety-blade dispenser of claim 9, wherein the confirmation label includes electronically scannable code, the electronically scannable code containing at least one of patient information and surgical procedure information.

12. The safety-blade dispenser of claim 11, wherein the electronically scannable code is one of a QR code and a bar code.

13. The safety-blade dispenser of claim 9, wherein the confirmation label includes at least one visual indicator conveying to a user the laterality of the surgical procedure.

14. The safety-blade dispenser of claim 13, wherein the at least one visual indicator includes at least one of words and color.

15. The safety-blade dispenser of claim 11, further comprising a packaging assembly adapted to receive the safety-blade dispenser prior to the surgical procedure.

16. The safety-blade dispenser of claim 15, wherein said packaging assembly comprises a first transparent sterile pouch, a second transparent sterile pouch, and a non-sterile outer container.

17. The safety-blade dispenser of claim 16, wherein said safety-blade dispenser is sealed within said first transparent sterile pouch, which is sealed within said second transparent sterile pouch, which is placed within said non-sterile outer container.

18. The safety-blade dispenser of claim 17, wherein said non-sterile outer container includes a transparent window.

19. The safety-blade dispenser of claim 18, wherein said safety-blade dispenser is placed within said packaging assembly such that said electronically scannable code is scannable through said first transparent sterile pouch, said second transparent sterile pouch, and said transparent window while contained within said packaging assembly.

* * * * *